ization of carbon nanotube based super-structures", AIP Conf. Proc. 1650, 1230, Jul. 20-25, 2014, pp. 1-8.

(12) United States Patent
Wincheski et al.

(10) Patent No.: US 10,139,345 B2
(45) Date of Patent: Nov. 27, 2018

(54) MAGNETIC AND RAMAN BASED METHOD FOR PROCESS CONTROL DURING FABRICATION OF CARBON NANOTUBE BASED STRUCTURES

(71) Applicant: The United States of America as represented by the Administrator of the National Aeronautics and Space Administration, Washington, DC (US)

(72) Inventors: Russell A. Wincheski, Williamsburg, VA (US); Jae-Woo Kim, Newport News, VA (US); Godfrey Sauti, Yorktown, VA (US); Emilie J. Siochi, Newport News, VA (US); Phillip A. Williams, Chesapeake, VA (US)

(73) Assignee: THE UNITED STATES OF AMERICA AS REPRESENTED BY THE ADMINISTRATOR OF NASA, Washington, DC (US)

( * ) Notice: Subject to any disclaimer, the term of this patent is extended or adjusted under 35 U.S.C. 154(b) by 401 days.

(21) Appl. No.: 14/873,646

(22) Filed: Oct. 2, 2015

(65) Prior Publication Data
US 2016/0103071 A1  Apr. 14, 2016

Related U.S. Application Data

(60) Provisional application No. 62/061,849, filed on Oct. 9, 2014.

(51) Int. Cl.
| G01N 21/65 | (2006.01) |
| G01N 27/72 | (2006.01) |
| B29C 37/00 | (2006.01) |
| C01B 32/168 | (2017.01) |
| B82Y 40/00 | (2011.01) |
| G01N 21/21 | (2006.01) |
| G01N 21/84 | (2006.01) |

(52) U.S. Cl.
CPC ........... *G01N 21/65* (2013.01); *C01B 32/168* (2017.08); *B82Y 40/00* (2013.01); *C01B 2202/08* (2013.01); *G01N 21/21* (2013.01); *G01N 2021/8416* (2013.01)

(58) Field of Classification Search
CPC ........... G01N 21/65; G01N 2021/8416; G01N 21/21; C01B 32/168; C01B 2202/08; B82Y 40/00
USPC .......................................... 264/408; 324/244
See application file for complete search history.

(56) References Cited

PUBLICATIONS

Zamora-Ledezma, et al., Anisotropic Thin Films of Single-Wall Carbon Nanotubes from Aligned Lyotropic Nematic Suspensions, Nano Letters 2008; 8(12): 4103-4107.*

De Volder, M. F. et al., "Carbon Nanotubes: Present and Future Commercial Applications," Science, Feb. 2013, pp. 535-539, vol. 339 (6119).
Chou, T.-W. et al., "An Assessment of the Science and Technology of Carbon Nanotube-Based Fibers and Composites," Composites Science and Technology, 2010, pp. 1-19, vol. 70.
Cheng, Q. et al., "Functionalized Carbon-Nanotube Sheet/Bismaleimide Nanocornposites: Mechanical and Electrical Performance Beyond Carbon-Fiber Composites," Small, 2010, pp. 763-767, vol. 6(6).
Cheng, Q. et al., "High Mechanical Performance Composite Conductor: Multi-Walled Carbon Nanotube Sheet/Bismaleimide Nanocomposites," Advanced Functional Materials, 2009, pp. 3219-3225, vol. 19.
Lin, Y. et al., "Purification of Carbon Nanotube Sheets," Advanced Engineering Materials, 2014, pp. 1-15.
Sun, K.J., et al, "Magnetic Property Measurements on Single Wall Carbon Nanotube Polyimide Composites," Journal of Applied Physics, 2008, pp. 023908-1-023908-6, vol. 103(2).
Cullity, B.D., "Superparamagnetlsm in Fine Particles," in "Introduction to Magnetic Materials," M. Cohen, Editor,1972, Addison-Wesley: Philippines, p. 410-418.
Dresselhaus, M.S. et al., "Raman Spectroscopy of Carbon Nanotubes," Physics Reports, 2005, pp. 47-99, 409(2).
Reich, S. et al., "Raman Spectroscopy of Graphite," Phil. Trans. R. Soc. Land. A, 2004, pp. 2271-2288, vol. 362.
Anglaret, E. et al., "Raman Resonance and Orientational Order in Fibers of Singie-Wali Carbon Nanotubes," Physical Review B, 2002, pp. 165426-1-165426-7, vol. 65.
Zamora-Ledezma, C. et al., "Anisotropic Thin Films of Single-Wall Carbon Nanotubes from Aligned Lyotropic Nematic Suspensions," Nano Letters, 2008, pp. 4103-4107, vol. 8(12).
Zamora-Ledezma C. et al., "Orientational Order of Single-Wall Carbon Nanotubes in Stretch-Aligned Photoluminescent Composite Films," Physical Review B, 2009, pp. 113407-1-113407-4, vol. 80(11).
Cronin, S.B. et al., "Measuring the Uniaxial Strain of Individual Single-Wall Carbon Nanotubes: Resonance Raman Spectra of Atomic-Force-Microscope Modified Single-Wall Nanotubes," Physical Review Letters, 2004, pp. 167401-1-167401-4, vol. 93(16).
Kumar, R. et al., "Raman Scattering of Carbon Nanotube Bundles Under Axial Strain and Straininduced Debundling," Physical Review B, 2007, pp. 155421, vol. 75(15).
Wincheski, B., et al., "Nondestructive evaluation techniques for development and characterization of carbon nanotube based superstructures", AIP Conf. Proc. 1650, 1230, Jul. 20-25, 2014, pp. 1-8.
Wincheski, B. et al., "Nondestructive Evaluation Techniques for Development and Characterization of Carbon Nanotube Based SuperStructures", Presentation Slides, Jul. 25, 2014, Review of Progress in Quantitative NDE, pp. 1-22, Boise, Idaho.

* cited by examiner

*Primary Examiner* — Daniel McCracken
(74) *Attorney, Agent, or Firm* — Andrea Z. Warmeier; Robin W. Edwards; Mark P. Dvorscak

(57) ABSTRACT

A method of fabricating composite structures comprising carbon nanotubes. The method including providing a nanotube starting material, forming the composite structure with the nanotube starting material and monitoring at least a magnetic or Raman property of the composite structure while forming the composite structure.

20 Claims, 26 Drawing Sheets

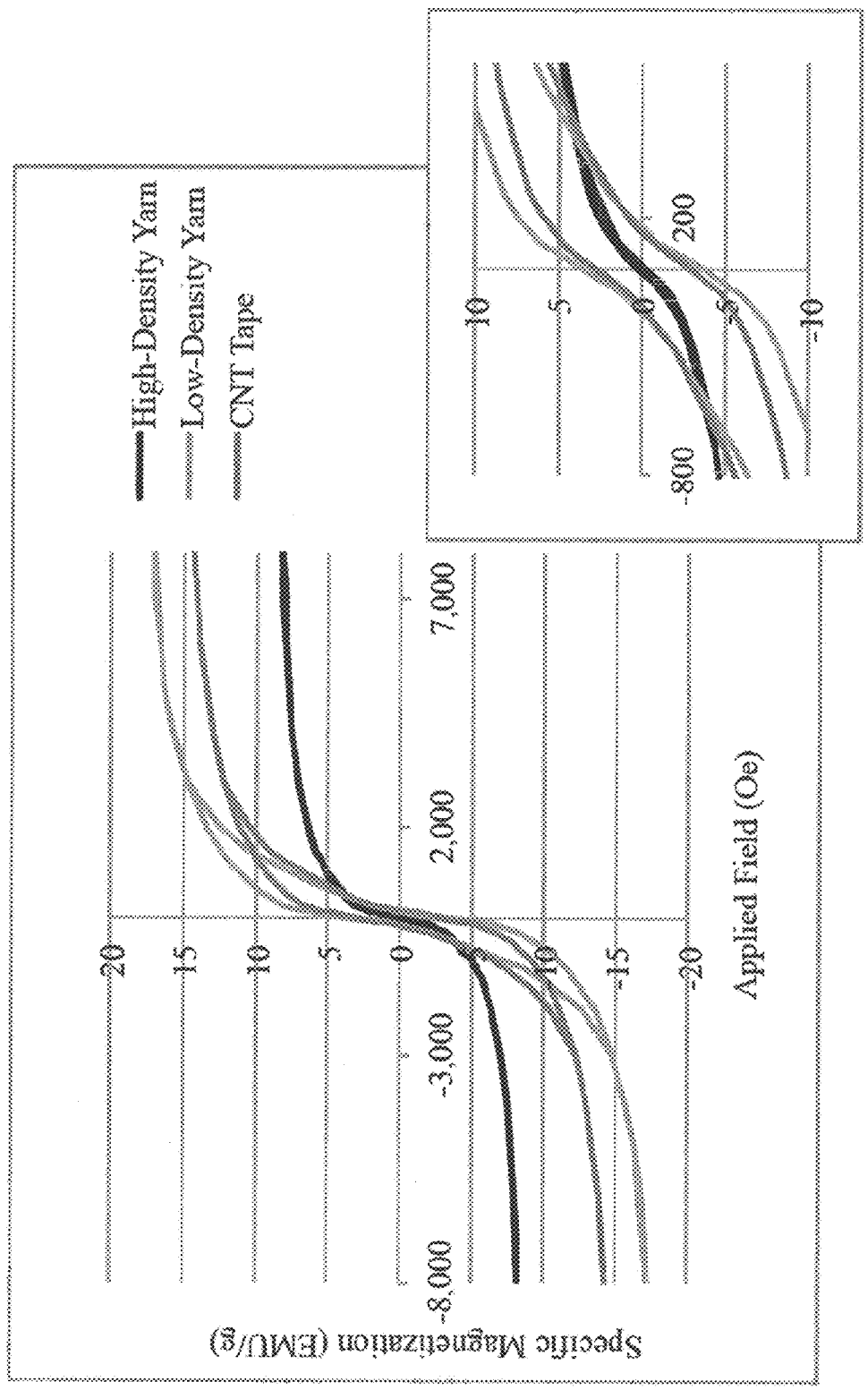

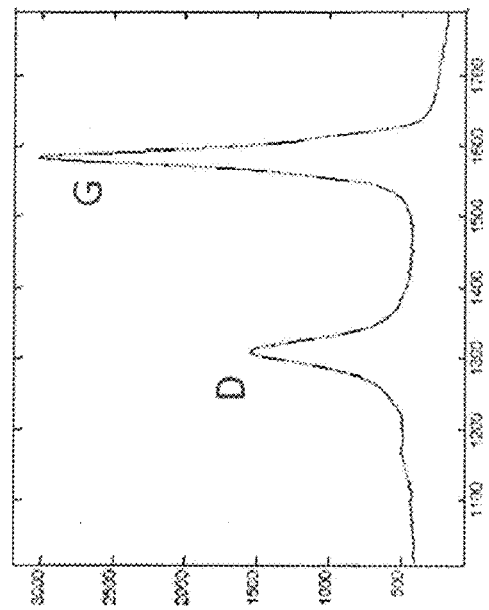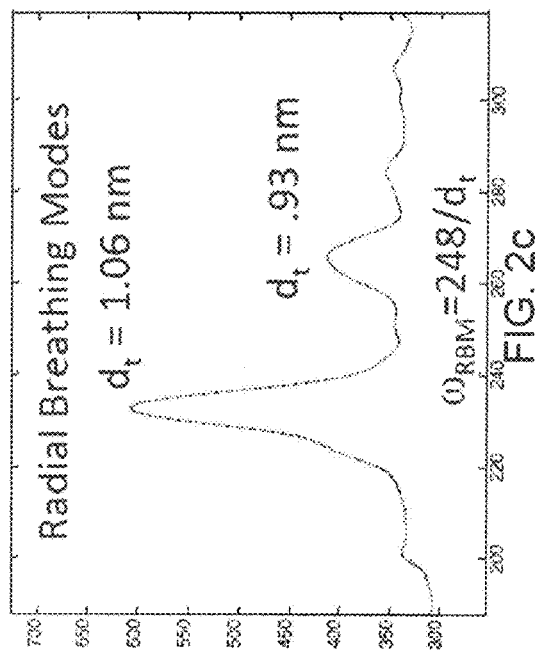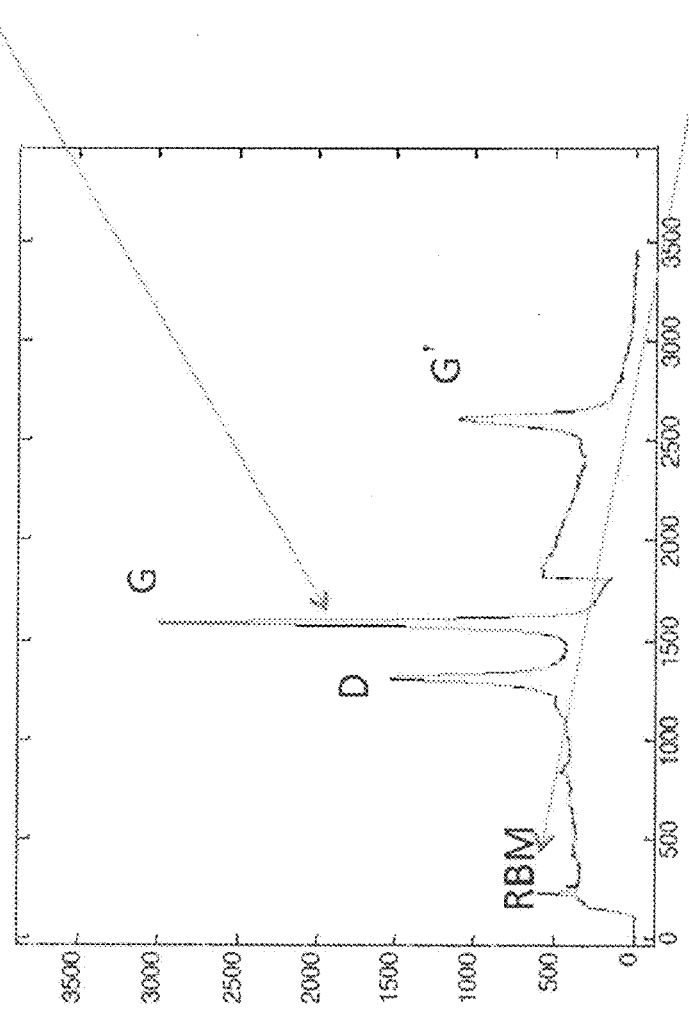
FIG. 2a
FIG. 2b
FIG. 2c

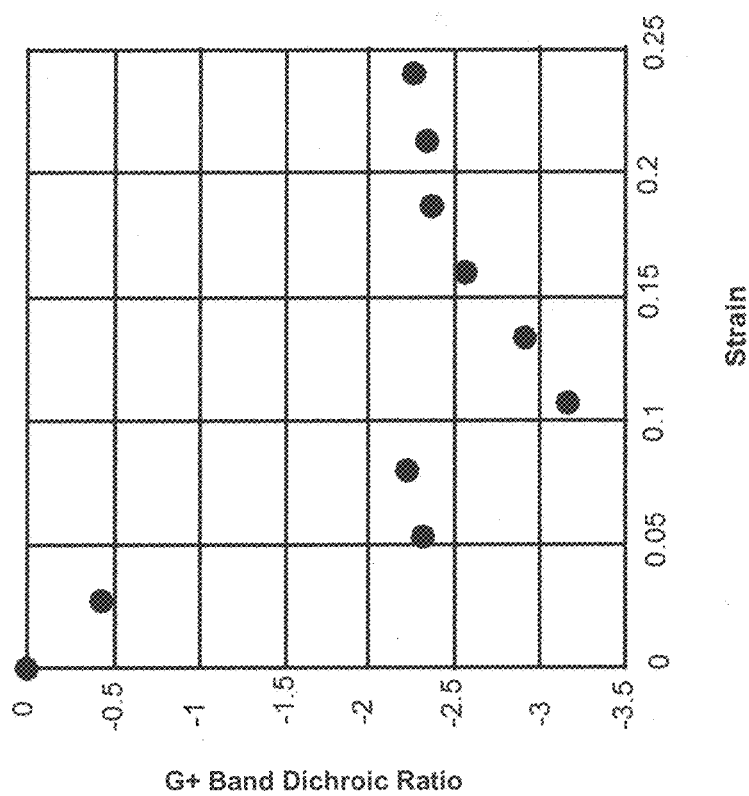
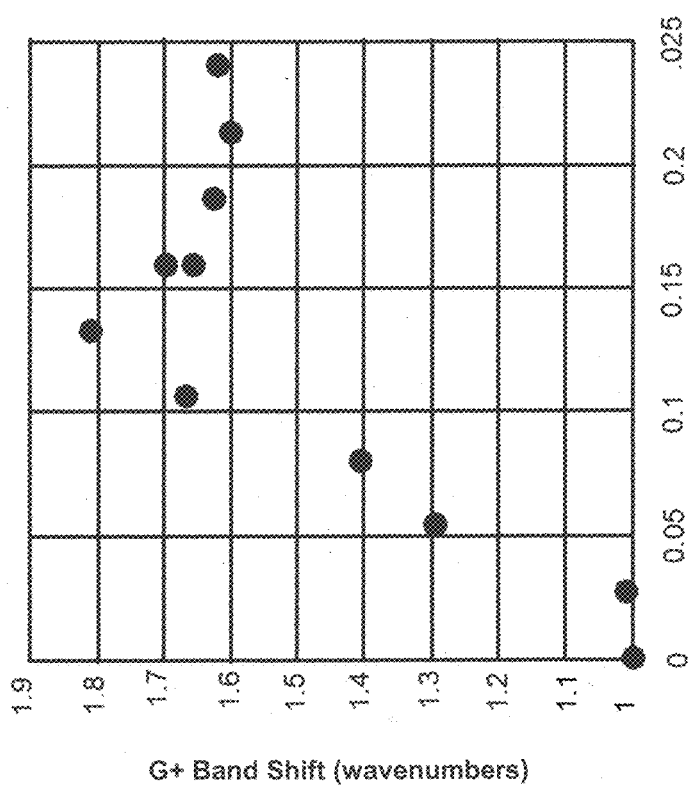
Fig. 4a
Fig. 4b

US 10,139,345 B2

MAGNETIC AND RAMAN BASED METHOD FOR PROCESS CONTROL DURING FABRICATION OF CARBON NANOTUBE BASED STRUCTURES

CROSS REFERENCE TO RELATED PATENT APPLICATION

This application claims the benefit of priority to U.S. Provisional Patent Application Ser. No. 62/061,849, filed on Oct. 9, 2014, which is incorporated herein by reference in its entirety.

STATEMENT REGARDING FEDERALLY SPONSORED RESEARCH OR DEVELOPMENT

The invention described herein was made in the performance of work under a NASA contract and by employees of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor elected not to retain title.

BACKGROUND OF THE INVENTION

Recently, multiple commercial vendors have developed the capability for the production of large-scale quantities of high-quality carbon nanotube (CNT) sheets and yarns. While the materials have found use in electrical shielding applications, development of structural systems composed of a high volume fraction of carbon nanotubes is still lacking.

The use of carbon nanotube based materials for structural applications continues to be rare in spite of the unique material properties of individual carbon nanotubes. Cost, availability, and processing difficulties have limited most work to the development of low volume fraction carbon nanotube polymer composites. While even a low volume fraction of carbon nanotubes has been found to be beneficial in increasing conductivity and strength compared to the neat polymers, structural properties have yet to approach those of state-of-the-art carbon fiber based composites.

BRIEF SUMMARY OF THE INVENTION

The present inventors have discovered methods of fabricating structural nanotube composites with strength-to-weight ratio exceeding current state-of-the-art carbon fiber composites. Commercially available carbon nanotube sheets, tapes, and yarns may be used as starting materials for processing into high volume fraction carbon nanotube-polymer nanocomposites. Nondestructive evaluation techniques are applied for material characterization and process control. These techniques include magnetic characterization of the residual catalyst content in the nanotubes; Raman scattering characterization of nanotube diameter, defect ratio, and nanotube strain; and polarized Raman scattering for characterization of nanotube alignment.

One embodiment is a method of fabricating composite structures comprising carbon nanotubes. The method includes providing a nanotube starting material, forming the composite structure with the nanotube starting material and monitoring at least a magnetic or Raman property of the composite structure while forming the composite structure.

Another embodiment is a composite structure comprising carbon nanotubes made by the methods disclosed herein.

These and other features, advantages, and objects of the present invention will be further understood and appreciated by those skilled in the art by reference to the following specification, claims, and appended drawings.

BRIEF DESCRIPTION OF THE SEVERAL VIEWS OF THE DRAWINGS

The accompanying drawings, which are incorporated herein and constitute part of this specification, illustrate exemplary embodiments of the invention, and together with the general description given above and the detailed description given below, serve to explain the features of the invention.

FIG. 1a is a plot of the specific magnetization as a function of applied field for three different carbon nanotube starting materials;

FIG. 1b is a plot of a portion of the data from FIG. 1a;

FIG. 2a is a Raman spectrum for a carbon nanotube sheet according to an embodiment of the present invention;

FIG. 2b is a plot of a portion of the Raman spectrum from FIG. 2a;

FIG. 2c is a plot of a portion of the Raman spectrum from FIG. 2a;

FIG. 4a is a plot of strain-induced changes in alignment measured by Raman dichroic ratio and 4b is a plot of strain measured by shift in the G+ band position for a carbon nanotube sheet according to an embodiment of the present invention;

FIG. 14b is a higher magnification scanning electron micrograph of the sheet of FIG. 14a;

FIG. 17b is a plot illustrating the G+ downshift of the carbon nanotube of FIG. 17a;

DETAILED DESCRIPTION OF THE INVENTION

Figure 3:
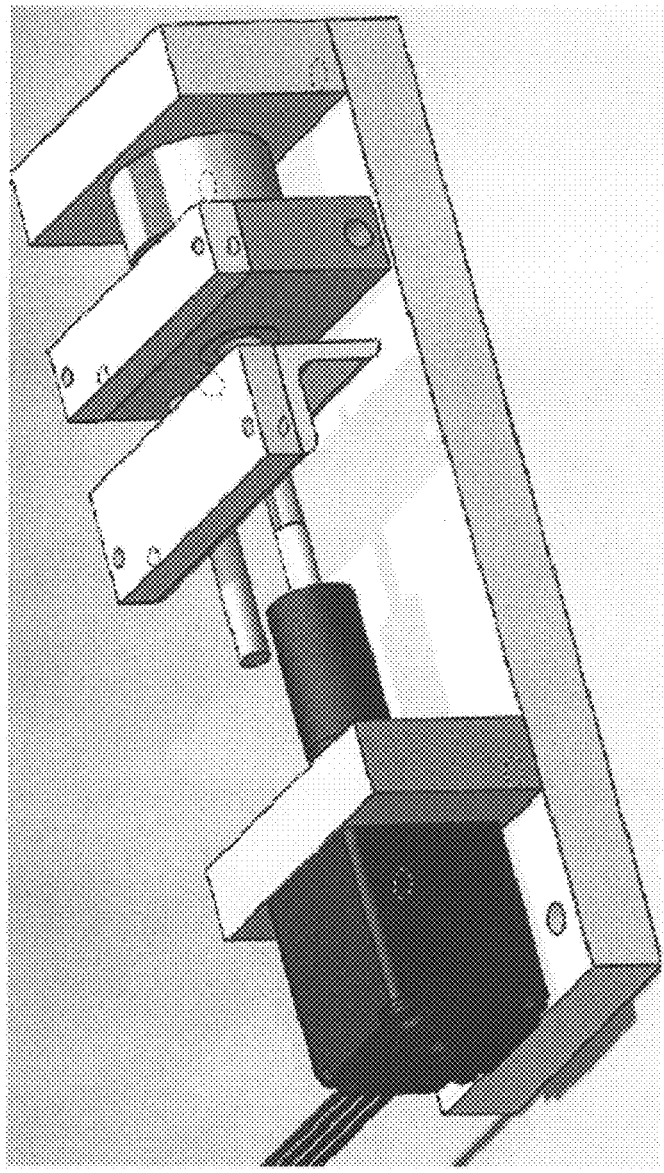
FIG. 3 is a side perspective drawing of an apparatus for in-situ measurements of carbon nanotube based materials under an applied strain.

For purposes of description herein, it is to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The word "exemplary" is used herein to mean "serving as an example, instance, or illustration." Any implementation described herein as "exemplary" is not necessarily to be construed as preferred or advantageous over other implementations.

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Recent high volume fraction nanotube composites have been demonstrated to yield mechanical properties competitive with carbon fiber composites. This work capitalized on a nanotube synthesis technique that produces large quantities of high-purity entangled carbon nanotubes in sheet and yarn formats. Commercially available from Nanocomp Technologies, Inc., the nanotube materials are fabricated using a continuous floating catalyst chemical vapor deposition technique in which a carbon fuel source and iron catalyst are continuously added at one end of the reactor and a carbon nanotube web is continuously produced at the other end. The nanotube web is condensed on a conveyor belt or captured on a spindle to create nanotube sheets and yarns, respectively. The various embodiments may use these materials as a starting point to produce a structural nanotube composites with strength-to-weight ratios exceeding current carbon fibers composites.

A side effect of prior methods to create nanotube sheets and yarns is that nanoscale catalyst particles, typically coated in an amorphous carbon shell, become embedded in the nanotube product. While purification steps can be pursued to remove the catalyst in post-processing, these steps are typically costly, time consuming, and potentially damaging to the carbon nanotubes themselves. In addition, the particles can provide entanglement points to increase the load transfer between individual nanotubes in the superstructure. A small but non-zero quantity of these particles may therefore be beneficial in achieving optimal mechanical properties in a structural nanotube composite. As such, a detailed characterization of the percentage and size of the catalyst particles in the nanotube sheets and yarns is helpful for understanding and optimizing the mechanical properties of the resultant nanotube composite structure. As catalyst sources for nanotube growth are typically iron based, the inventors have discovered that a magnetic signature of the catalyst may be used to characterize the resulting carbon nanotube material.

FIG. 1a shows superconducting quantum interference device (SQUID) magnetometry results at 300 kelvin for three carbon nanotube source materials: a carbon nanotube tape, a low-density carbon nanotube yarn, and a high-density carbon nanotube yarn. The full hysteresis loops illustrated in FIG. 1a show that the change in specific magnetization is directly related to weight percent of residual catalyst. FIG. 1b is a close up view of a portion of FIG. 1a. FIG. 2b demonstrates that changes in the coercive force provide insight into the size of residual catalyst particles. The data, summarized in Table 1 below, show that the magnetic properties of the three samples vary widely. The residual iron catalyst content can be estimated by dividing the saturation magnetization of the sample by that of pure iron, 218 emu/g. This gives a value of 7.9% by weight of Fe catalysts in the low-density yarn but only 3.7% in the high-density yarn. Also, the coercivities of the samples are markedly different. The CNT tape and low-density yarn show a high coercive force associated with small-diameter, potentially single-domain, Fe particles. The high-density yarn, however, has very little coercivity. It is believed that the size of the iron particles in the high-density yarn is beneath the critical diameter $D_p$ for stable magnetic domains to form at 300 Kelvin. Different reactor conditions are used in the growth of the different nanotube sources and varying conditions are likely the cause of the different magnetic signatures of the samples. This magnetic technique may be used in quality control of the nanotube sources as well as in process monitoring and optimization of the reactor conditions during nanotube growth.

TABLE 1

| Material Under Test | Saturation Magnetization (emu/g) | Coercive Force (Oe) | Remanence (emu/g) |
| --- | --- | --- | --- |
| Nanotube Tape | 14.2 | 138 | 2.74 |
| Low-Density Yarn | 17.2 | 162 | 3.65 |
| High-Density Yarn | 8.17 | <10 | <0.2 |

Individual carbon nanotubes have exceptional mechanical properties along the axis of the nanotube with theoretical ultimate strength and elastic modulus as high as 100 GPa and 1000 GPa, respectively. Composite nanotube structures will have a knock-down from these nanoscale properties. However, material processing steps according to the methods herein minimize this knock-down. Two factors that reduce macroscopic properties as compared to those at the nanoscale are alignment of the nanotubes along the stress axis and strain transfer between individual nanotubes in the superstructure. Raman spectroscopy provides an experimental technique for the nondestructive monitoring of these two important processing parameters during processing. Based on this monitoring, the fabrication process parameters may be adjusted to optimize the desired properties.

Figure 12A:
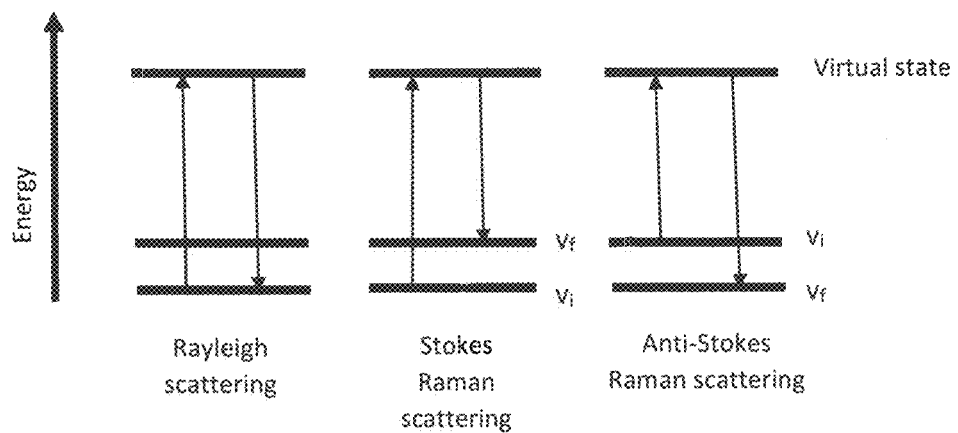
FIG. 12a is an energy diagram illustrating Rayleigh scattering, Stokes Raman scattering and anti-Stokes scattering.
Figure 12B:
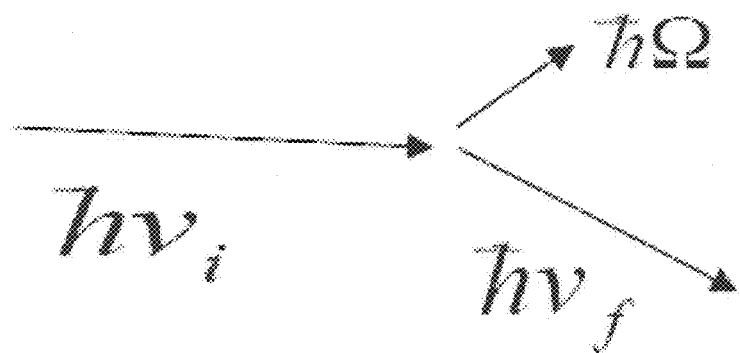
FIG. 12b is a ray diagram illustrating Stokes/anti-Stokes scattering.

Raman spectroscopy, as shown in FIGS. 12a and 12b, is a technique in which vibrational modes of a crystal or molecule are excited by the inelastic scattering of light. Typically, a narrow-wavelength laser source is directed at the material under test. As the photons impinge on the sample, a vibrational (phonon) mode of the crystal can be excited, leading to a loss of energy of the light that is equivalent to the energy of the excited phonon mode. The scattered and reflected light is collected by a spectrometer, and the wavelength spectrum measured. The Raman spectrum is then plotted as intensity versus Raman shift where the Raman shift is defined as $$\Delta w = \left( \frac{1}{\lambda_0} - \frac{1}{\lambda_1} \right) \quad (1)$$

Here, $\Delta w$ is the Raman shift (typically reported in units of $cm^{-1}$), $\lambda_0$ is the excitation wavelength and $\lambda_1$ is the wavelength of the scattered light.

FIGS. 2a-2c illustrate the Raman spectrum acquired on a carbon nanotube sheet. The data were acquired using a Kaiser Raman RXN1™ Microprobe configured with a 785 nm laser at 100 mW output power. The prominent peak at ~1580 $cm^{-1}$ is related to the C—C bond stretching between the two dissimilar carbon atoms in the graphene unit cell. Commonly referred to as the G band, this peak in a carbon nanotube consists of two sub components, G+ and G−, associated with vibrations along the nanotube axis (longitudinal optical phonon mode) and vibrations along the circumferential direction of the nanotube (transverse optical phonon mode), respectively. The second strongest peak in the Raman spectrum of FIGS. 2a-2c occurs at ~1350 $cm^{-1}$ and is a disorder-induced mode (so-called D band) involving elastic phonon scattering from a defect site. The ratio of the intensity of the disorder-induced D band at 1350 $cm^{-1}$ to that of the G band can be used as a measure of nanotube quality in the material. The two other prominent features in the Raman spectrum of FIGS. 2a-2c occur at approximately 2700 $cm^{-1}$ and near 250 $cm^{-1}$. The strong peak near 2700 $cm^{-1}$ is alternatively referred to as the G' peak (being a strong symmetry allowed peak in perfect graphite crystals) or the 2D peak (being an overtone of the D peak). Like the D peak, it arises from a second-order process involving phonon scattering. In the 2D (G') peak, the process involves a double-resonance scattering by two phonons as opposed to a phonon and defect as described above for the D band. The set of peaks near 250 $cm^{-1}$ are a result of radial breathing modes (RBM) of the single walled nanotubes in the sample. The RBM, like the G mode, is a first-order Raman process. In the RBM all carbon atoms move coherently in the radial direction. The wave number of this mode is inversely proportional to the diameter of the single wall carbon nanotube being interrogated and is often used to calculate this quantity.

Figure 18A:
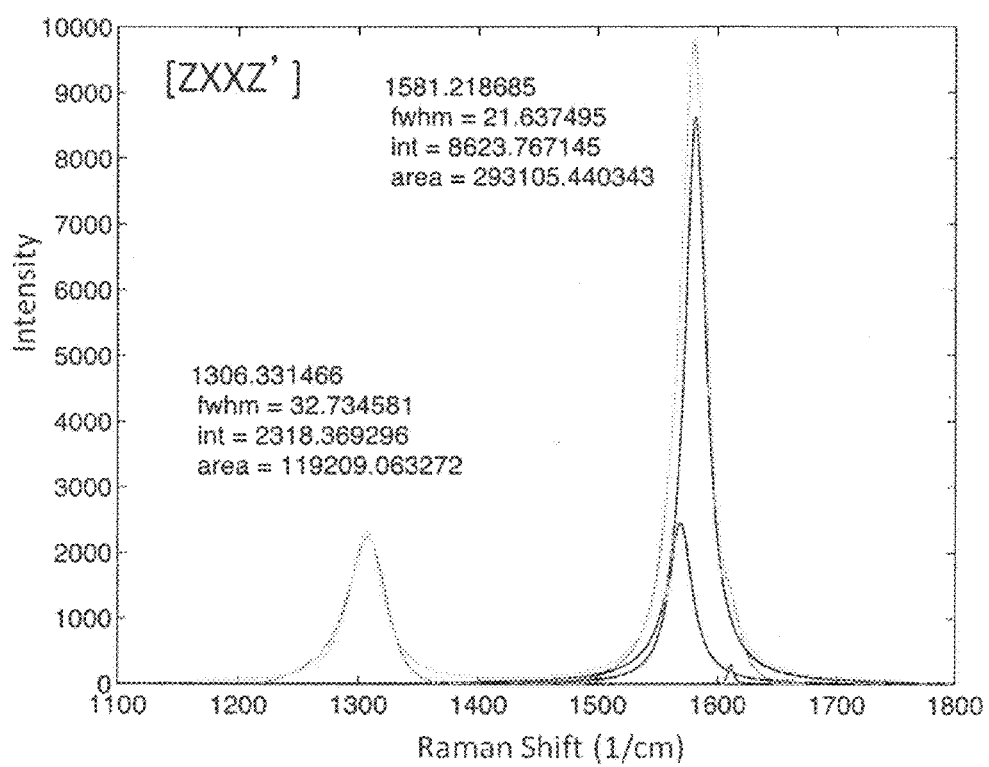
FIG. 18a is a Raman spectra of a nanotube sheet using ZXXZ' polarization.
Figure 18B:
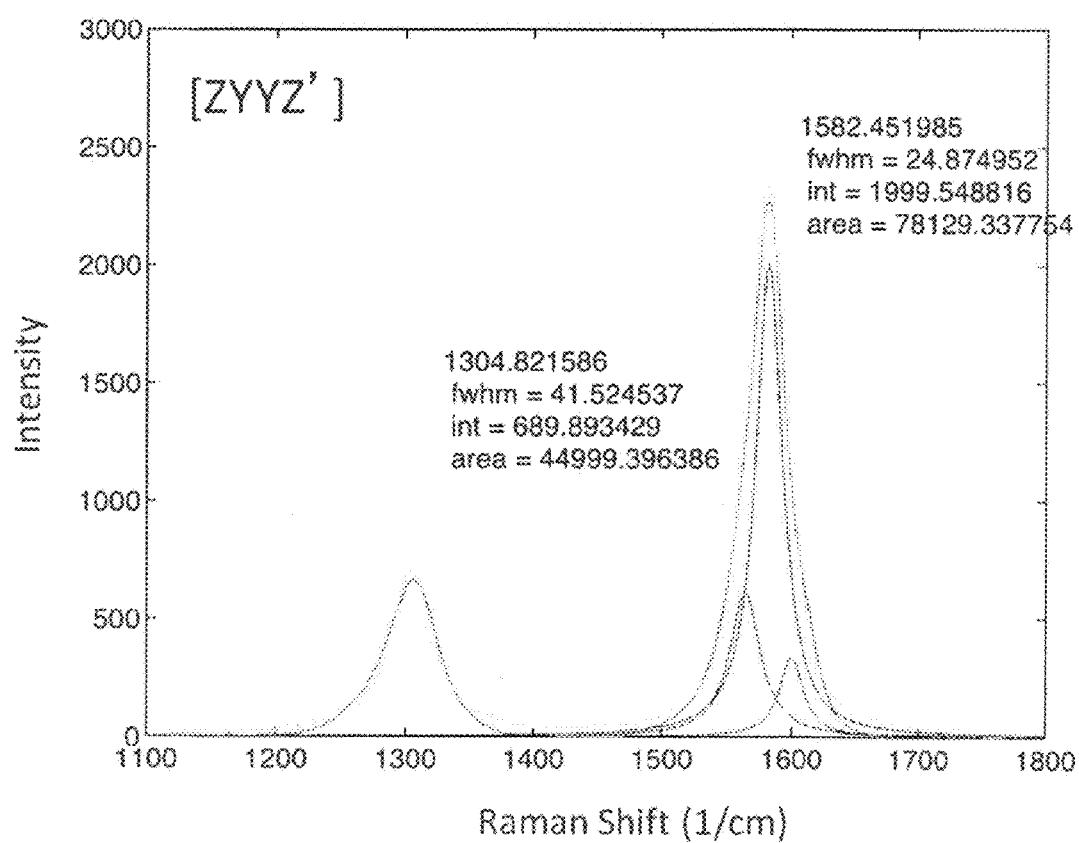
FIG. 18b is a Raman spectra of the nanotube sheet of FIG. 18a using ZYYZ' polarization.
Figure 18C:
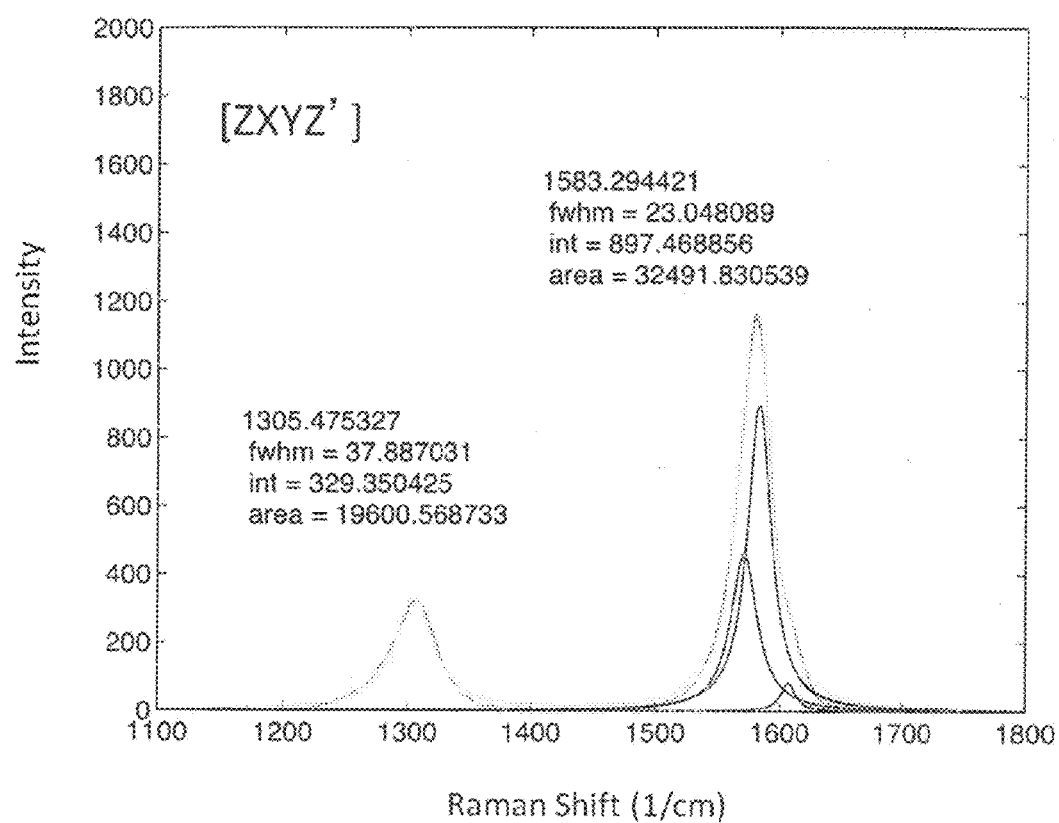
FIG. 18c is a Raman spectra of the nanotube sheet of FIG. 18a using ZXYZ' polarization.

Polarized Raman spectroscopy may be used characterize the alignment of individual nanotubes in nanotube based fibers, thin films and composites. The orientation distribution of the nanotubes can be described by the three-dimensional order parameter, S, $$S = \frac{1}{2}(3 \cos^2\beta - 1) \quad (2)$$

where $\beta$ is the angle between the nanotube and the measurement axes. Using the approximation that the Raman polarization tensor is non-negligible only for incident and scattered light parallel to the nanotube axis allows equation (2) to be rewritten in terms of the Raman intensities under three different polarization conditions, $$S = \frac{3I_{VV} + 3I_{VH} - 4I_{HH}}{3I_{VV} + 12I_{VH} + 8I_{HH}} \quad (3)$$

where $I_{VV}$ is Raman intensity for incident and scattered polarization parallel to main alignment direction; $I_{HH}$ is Raman intensity for incident and scattered polarization perpendicular to main alignment direction; and $I_{VH}$ is incident polarization parallel and scattered polarization perpendicular to main alignment direction In the experimental configuration, light was directed at the sample along the Z-axis and linearly polarized along either the X or Y axes. The sample lies in the XY plane with nominal alignment along the X-axis. The back reflected light from the sample is collected along the Z'-axis and passes through a second X/Y polarizer before reaching the spectrometer. Three polarization configurations, <ZXXZ'>, <ZYYZ'>, and <ZXYZ'>, are collected, as illustrated in FIGS. 18a-18c, where <ZXXZ'> corresponds to $I_{VV}$, <ZYYZ'> corresponds to $I_{HH}$ and <ZXYZ'> corresponds to $I_{VH}$ in equation 3 above. Three polarization configurations, <ZXXZ'>, <ZYYZ'>, and <ZXYZ'>, are used to calculate the order parameter as defined above. Following data acquisition, the Raman spectra are processed to isolate the G+ peak from the G band for each polarization configuration, and the intensities from these peaks are used as the inputs to equation (3) above.

Along with nanotube alignment, Raman scattering can be used to measure the strain on the individual nanotubes under test. As a nanotube is strained, there is an elongation of the carbon-carbon bonds, weakening the bond strength. The weaker bond strength results in a drop in energy of the G+ band and therefore less loss in energy of the Raman scattered light. The wavelength of the scattered light decreases closer to that of the excitation source and, by equation (1), a downshift in the G+ band is detected. Experimental evaluation of this effect has shown a downshift of the G+ band of 27.9 $cm^{-1}$/% strain. Assuming a CNT modulus of 1 TPa, this equates to a stress-induced downshift of 2.79 $cm^{-1}$/GPa for the G+ band.

FIG. 3 illustrates a solid model of a miniature load frame designed to study the strain-induced alignment of carbon nanotube materials as well as the strain transfer in a nanotube network. The system is designed to fit under the Raman microprobe described above while applying loads of up to 25 pounds to the material under test. The load frame is displacement-controlled by a stepper motor with minimum step size of 0.000125". The nominal gauge length of the samples was set to 0.75", resulting in a strain resolution of 167 micro-strain. A 25-pound load cell with accuracy of +/−0.0375 pounds was incorporated such that load-displacement curves of the material under test can be generated.

FIG. 4a illustrates experimental results for the dichroic ratio, $I_{xx}/I_{yy}$. The dichroic ratio is the ratio of the light intensity measured with parallel polarization ($I_{xx}$) to the intensity of the light measured with perpendicular polarization ($I_{yy}$). FIG. 4b illustrates the G+ band shift with strain for a carbon nanotube sheet placed under uniaxial strain up to 24% along the x-axis. The relative alignment, measured by the dichroic ratio, increases nearly linearly with strain up to 13% strain, after which there is a step decrease in alignment followed by a continued slight decrease with increasing strain. The nanotube strain, measured by the downshift in the G+ band peak position, follows a similar trend. The G+ band position decreases with increasing strain to a maximum change of −3.16 wave numbers at 11% strain.

During testing, the change in trending of the data at 16% strain was observed, and a second data set was acquired at this strain level to verify the results. Once the results were confirmed, the testing was continued up to a strain of 24%. At this point the sample was examined, while held at 24% strain, under the optical microscope on the Raman microprobe. The sample was scanned under the microscope using the sample stage driven by a stepper motor, and a failure site in the CNT sheet was observed, which is believed to have originated during the approach to 16% strain level. On examination, it was found that the failure was not complete and that a strand of the CNT sheet bridged the tear in the material. An optical photograph of the failure site and fiber bridging the tear is shown in FIG. 5.

Figure 5:
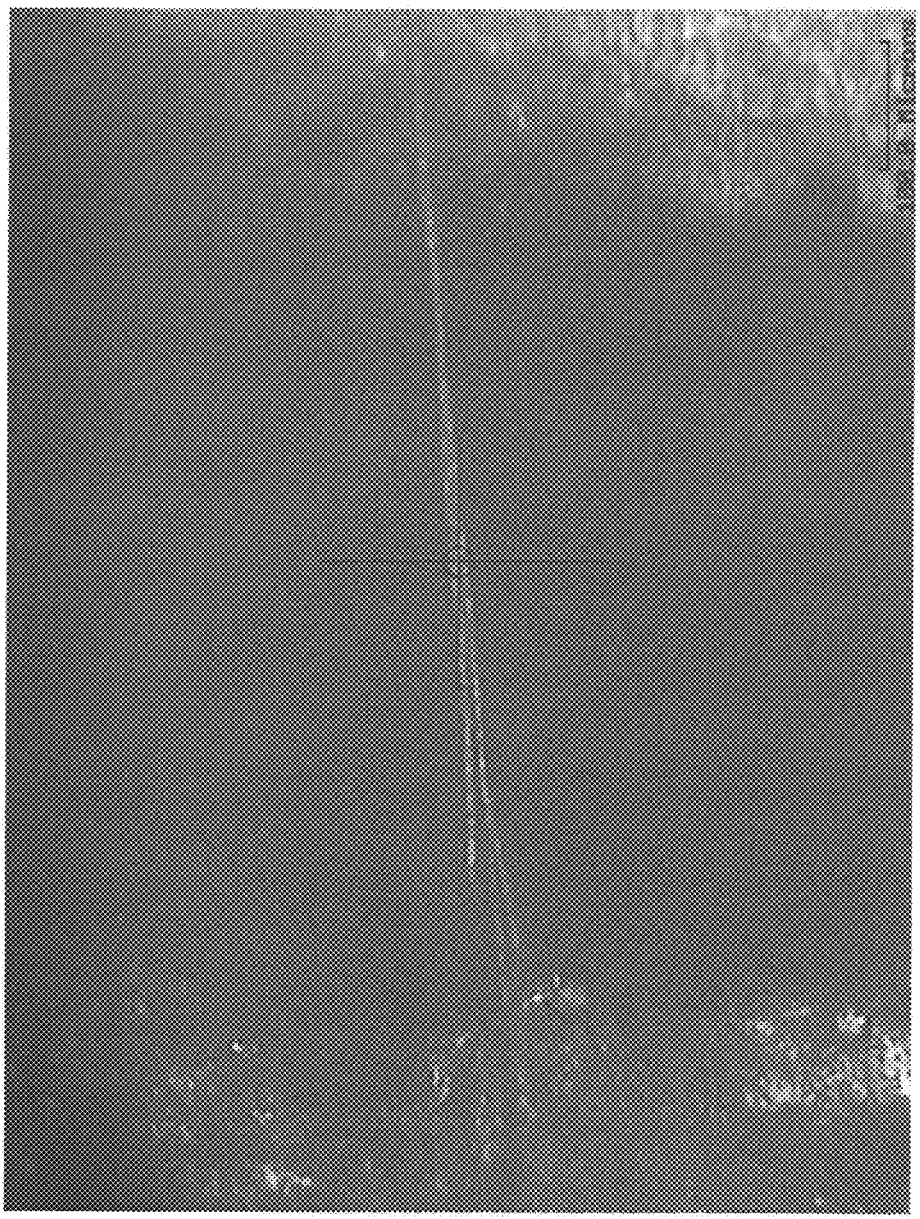
FIG. 5 is an optical micrograph of a fiber bridging a tear in nanotube sheet.

Analysis of the Raman signature of the fiber bridging the tear in the nanotube shown in FIG. 5 verified a high degree of strain-induced alignment and stress on the nanotube fiber. The dichroic ratio $I_{xx}/I_{yy}$ was measured as 9.98, an increase of more than 5-fold over the peak ratio away from the damage. Analysis of the G+ band peak position showed a downshift of 10.75 cm$^{-1}$, which equates to a stress level of 3.85 GPa for the individual nanotubes entangled in the fiber.

Another experimental study using the in-situ Raman load frame shown in FIG. 3 was performed to examine the effect of different carbon nanotube material formats and processing treatments on the alignment and nanotube strain transfer. Nanotube sheet material, supplied in tape format, and nanotube yarn material in both a low-density and high-density format were examined. In addition, the nanotube tapes were studied during a dry stretching process and during a solvent based stretching process in which the material was maintained in a methanol-wetted state during stretching. All processing of the yarn materials was performed under dry conditions. The results from this work are summarized in Table 2 below. In comparing the results of the three materials under dry stretching, it is apparent that the yarn material begins in a more aligned state and that strain-induced alignment has a smaller impact on the final order of the structure in the yarn based materials. This is because the processes used to produce the yarns involve drawing-out, consolidating and thus pre-aligning the carbon nanotube feed. While the order parameter of the tape was increased by more than 3 times, that of the high-density yarn was only increased by approximately 7%. Wetting of the material was found to increase the achievable alignment, but the load transfer between nanotubes was greatly reduced as indicated by the small wave number downshift of the wet stretch tape. The solvent wetting of the tape material during stretching possibly enabled an increase in the slippage of nanotubes past each other or an increase in the physical separation of the nanotubes within the material and thereby resulted in the observed reduction of load transfer between the nanotubes.

TABLE 2

| Material Under Test | Initial Raman Order Parameter | Maximum Raman Order Parameter Under Strain | Maximum Wave number Shift Under Strain |
| --- | --- | --- | --- |
| Dry Stretch Tape | 0.05 | 0.16 | 2.3 cm$^{-1}$ |
| Wet Stretch Tape | 0.05 | 0.20 | 0.9 cm$^{-1}$ |
| Low-Density Yarn | 0.15 | 0.25 | 1.5 cm$^{-1}$ |
| High-Density Yarn | 0.58 | 0.62 | 2.9 cm$^{-1}$ |

Carbon fiber reinforced (CFR) composite properties are not typically sufficient to enable single-stage-to-orbit (SSTO) vehicle designs for affordable access to space. However, carbon nanomaterials properties are typically superior to carbon fibers. Conventional nanostructured materials are available in useful quantities, but bulk properties are far below theoretical potential.

In practice, nanomaterials can be used as dopants only at low loading levels, yielding nanocomposites with mechanical properties inferior to state of the art CFR composites. Extremely high degrees of alignment and packing of CNTs may be required to achieve necessary structural property goals.

According the methods discussed herein commercially available carbon nanotube based fibers, yarns, and sheets may be used as starting materials to fabricate composite nanotube structures. Methods include aligning and joining nanomaterials physically and chemically, during and after the CNT manufacturing process to improve load transfer with minimal resin binder compared to state of the art epoxy composites. Computational molecular modeling may be used to provide insight into material parameters that affect structural performance and physical insight into molecular-level mechanisms that influence observed bulk-level behavior. With the methods disclosed herein, unconventional structural concepts based on low resin content nanocomposites may be explored in conjunction with systems analysis to determine systems benefits. Net shape fabrication methods for tailored nanocomposites may also be used. With the methods disclosed herein, meter-scale nanomaterials based structure with properties superior to CFR composites can be fabricated.

Figure 6:
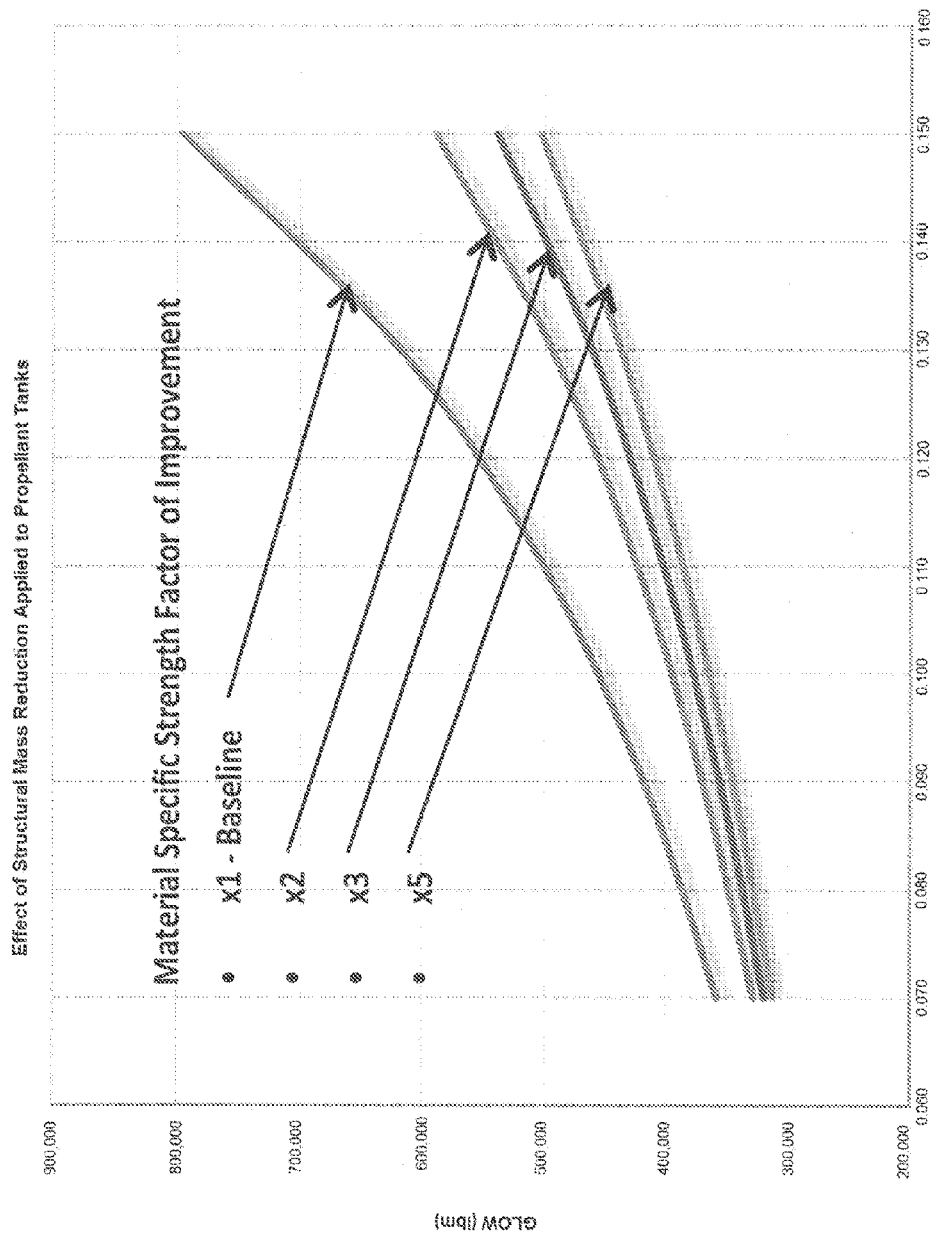
FIG. 6 is a plot illustrating the effect of structural mass reduction applied to propellant tanks according to an embodiment of the present invention.
Figure 7:
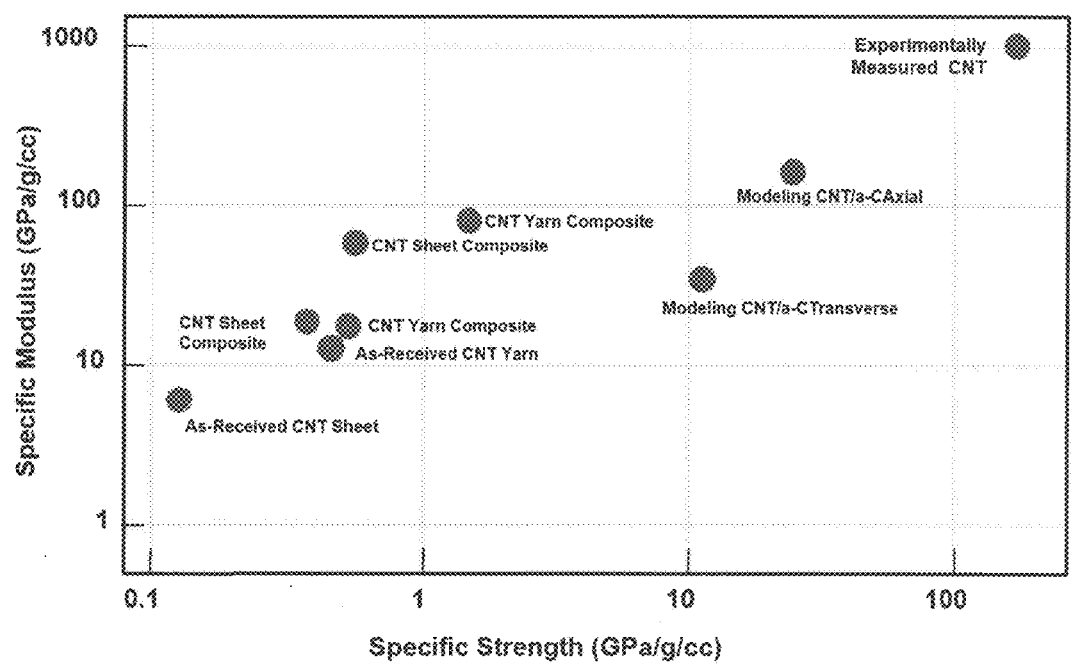
FIG. 7 is a plot illustrating the specific modulus as a function of specific strength comparing material of CNT sheets with experimentally measured CNT of the present invention.

FIG. 6 illustrates the effect of structural mass reduction applied propellant to tanks according to an embodiment. As illustrated in the figure, a 30% structural mass savings in gross liftoff weight (GLOW) may be achieved. FIG. 7 is a plot illustrating the specific modulus as a function of specific strength comparing commercial off the shelf materials with experimentally measured CNT of the present invention made by the methods disclosed herein.

Figure 8:
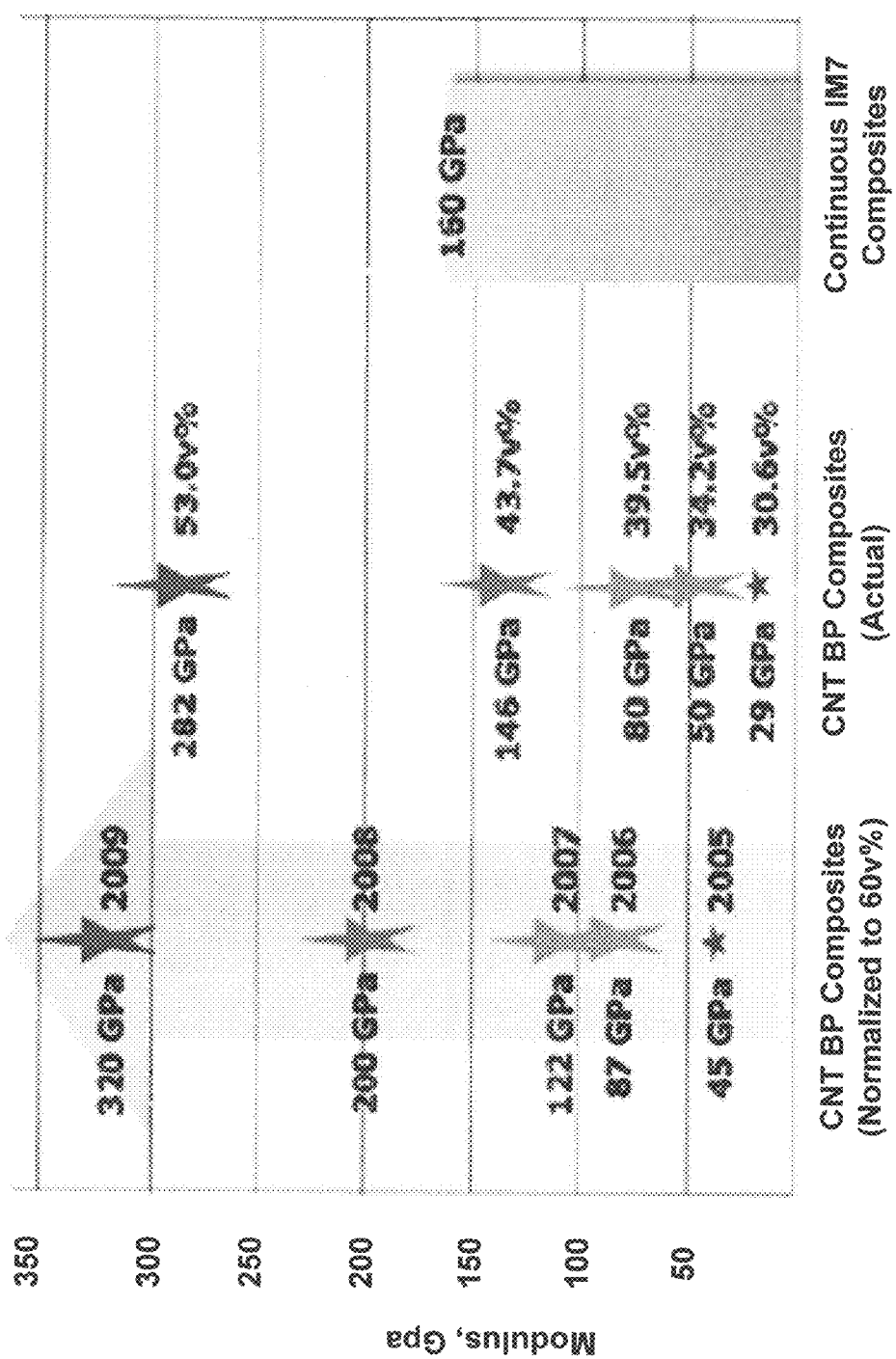
FIG. 8 is a plot comparing the nanotube composites.
Figure 9:
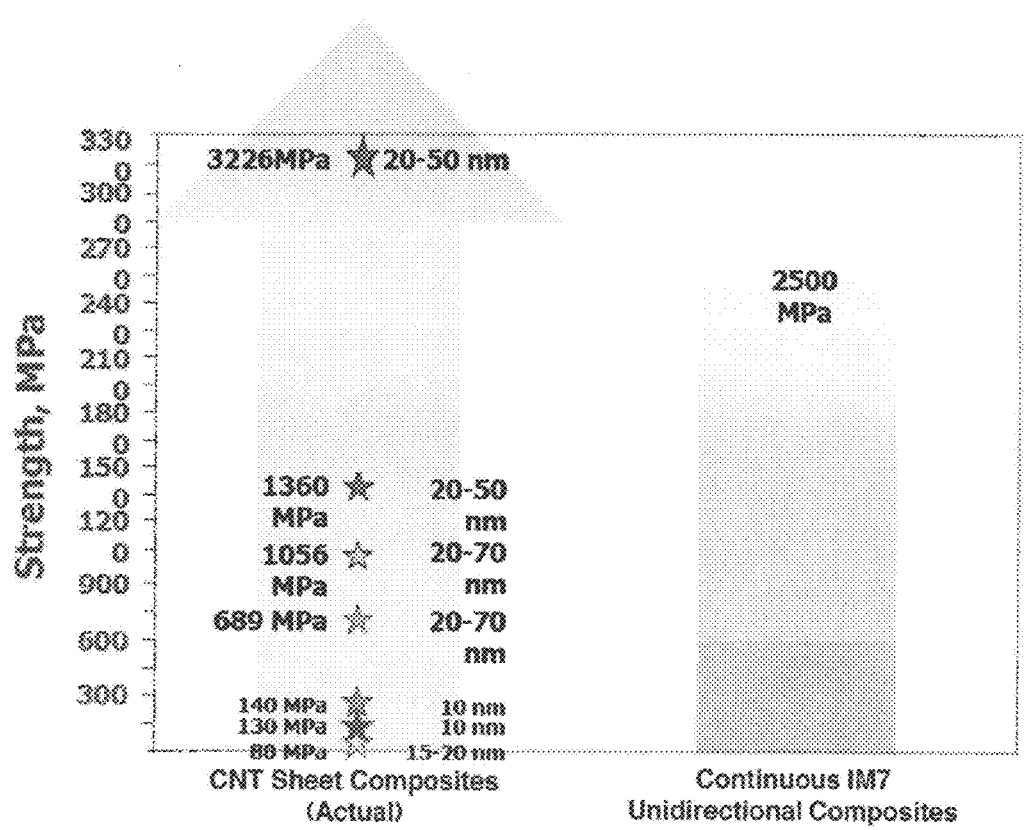
FIG. 9 is a plot comparing the strength of nanotube composites.

FIG. 8 is a plot comparing the modulus of conventional carbon nanotube composites and conventional carbon fiber composites with high performance laboratory scale nanotube composites. FIG. 9 is a plot comparing the strength of conventional carbon nanotube composites and conventional carbon fiber composites with high performance laboratory scale nanotube composites. As can be seen in FIGS. 8 and 9, nanotube composite materials at the laboratory scale have been shown to have superior modulus and strength to conventional materials. An embodiment disclosed here will enable optimization, quality control, and scale up these laboratory scale properties to scales required for use in structural applications.

Figure 10:
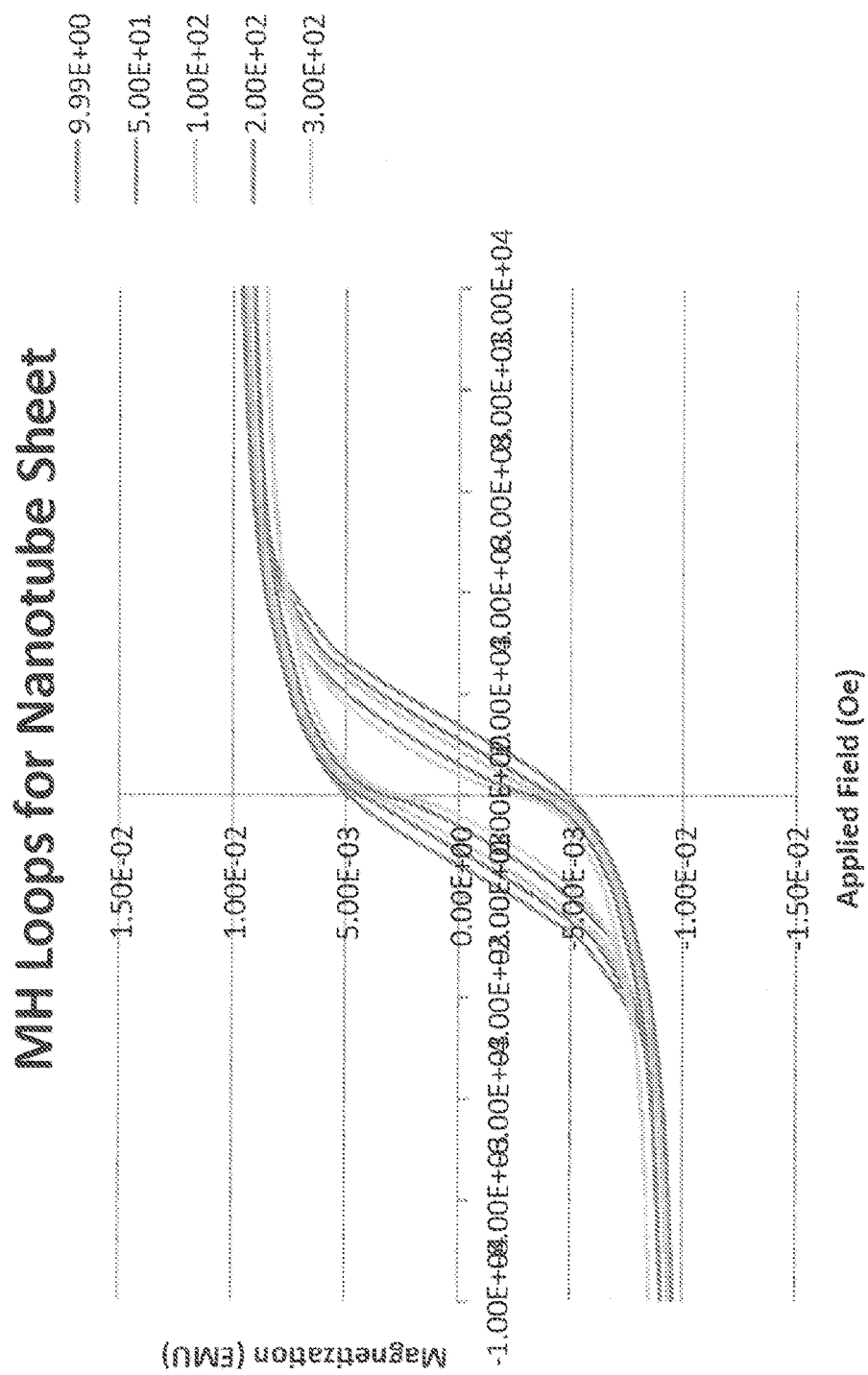
FIG. 10 is a plot illustrating magnetic hysteresis loops of nanotube sheet materials according to an embodiment of the present invention.
Figure 11:
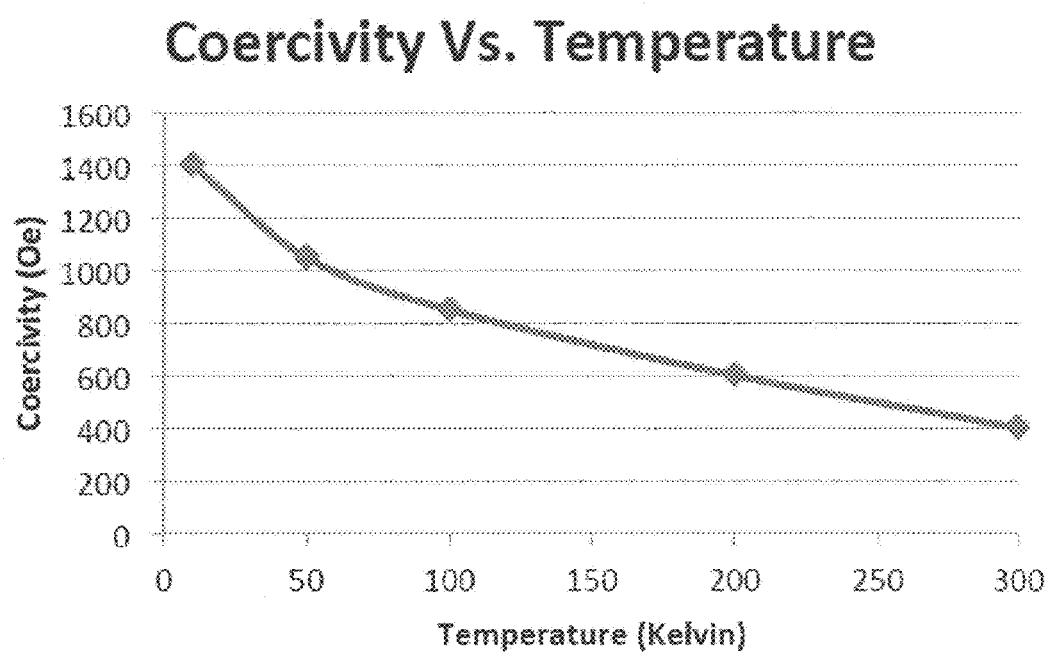
FIG. 11 is a plot illustrating the coercivity of nanotube sheet materials according to an embodiment of the present invention.

FIG. 10 is a plot illustrating magnetic hysteresis loops of nanotube sheet materials according to an embodiment. The hysteresis loops were measured with a superconducting quantum interference (SQUID) device. As discussed above, the saturation magnetization measures the volume fraction of the residual catalyst in the sample. FIG. 11 is a plot illustrating the coercivity of nanotube sheet materials according to an embodiment. The coercivity provides a measure of the catalyst particle size.

Figure 13A:
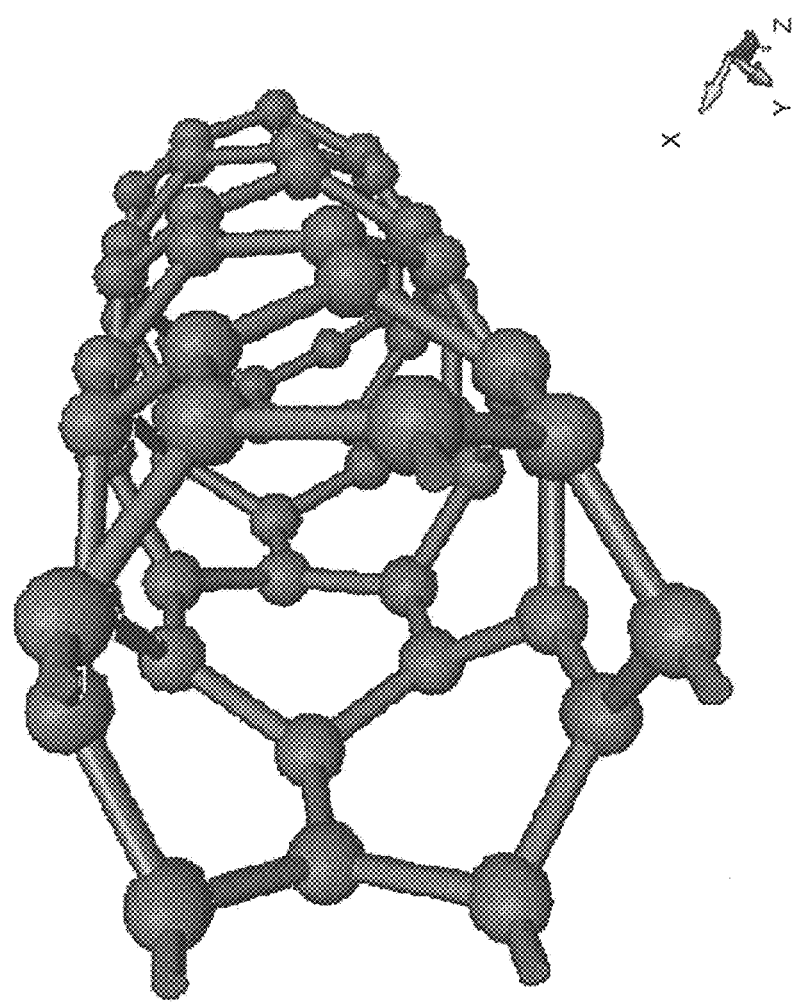
FIG. 13a is a top view first principle model of a single wall carbon nanotube using density functional theory.
Figure 13B:
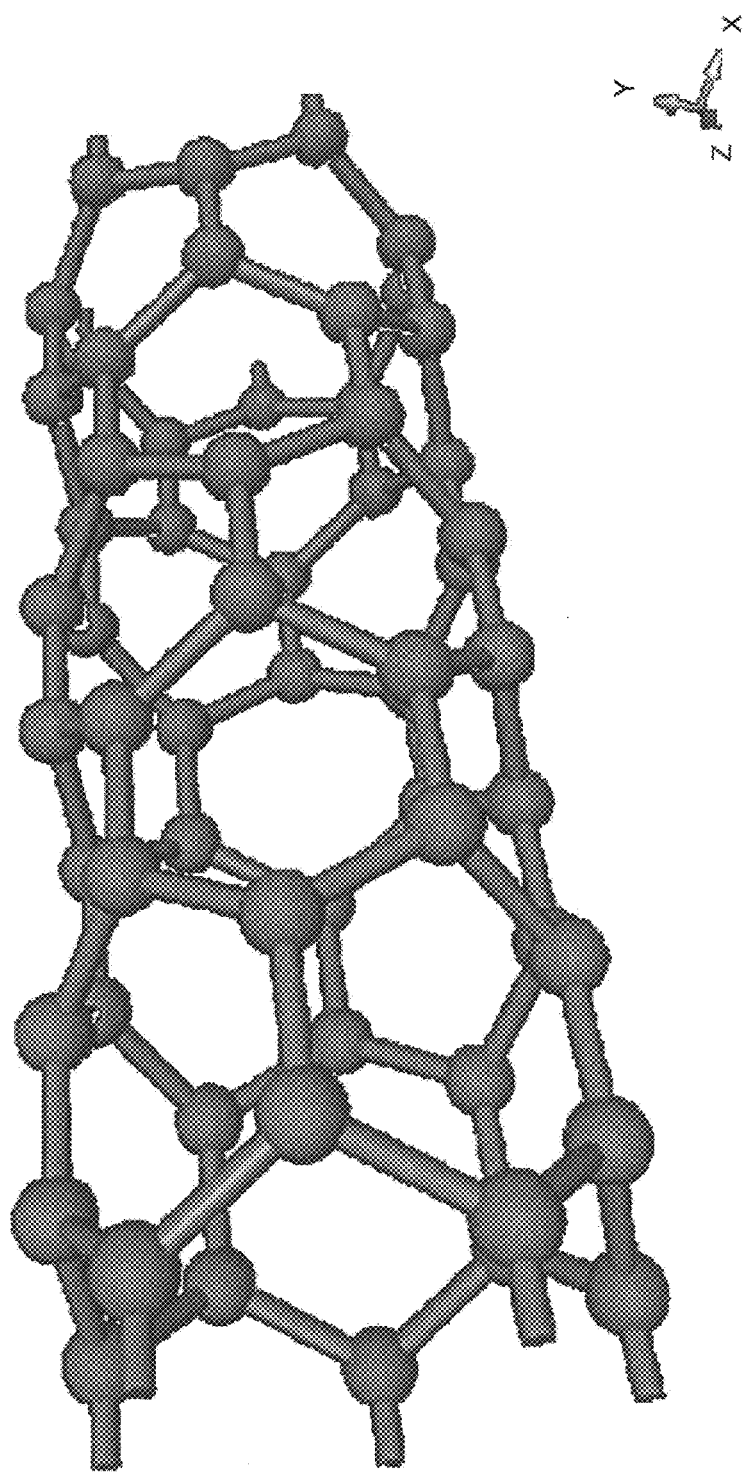
FIG. 13b is a side view first principle model of a single wall carbon nanotube using density functional theory.

FIG. 13a illustrates a top view first-principle model of a single wall carbon nanotube using density functional theory. FIG. 13b illustrates a side view first principle model of a single wall carbon nanotube using density functional theory. These figures clearly show the hexagonal graphene structure of the carbon nanotubes.

Figure 14A:
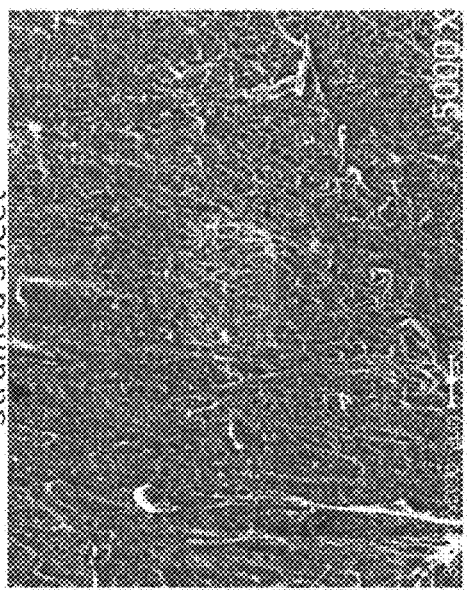
FIG. 14a is a scanning electron micrograph of a strained carbon nanotube composite sheet.
Figure 14B:
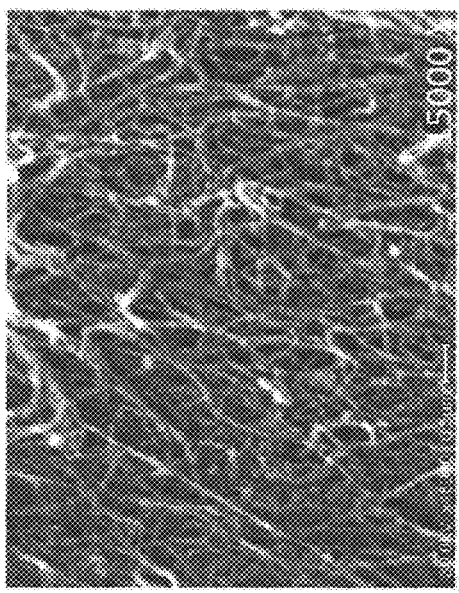
Figure 14C:
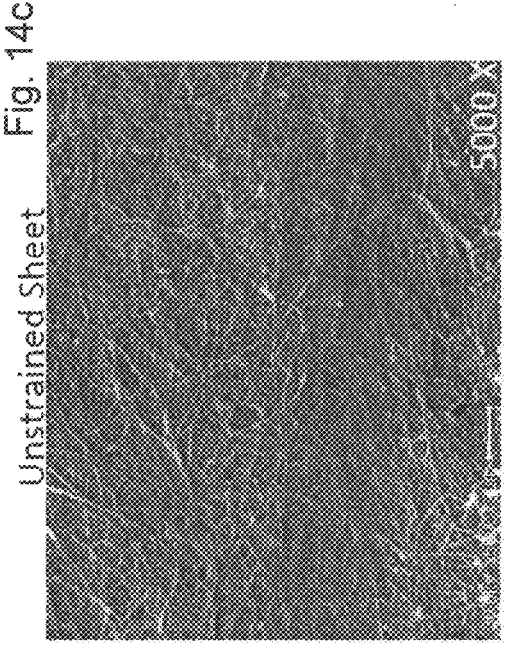
FIG. 14c is a scanning electron micrograph of an unstrained carbon nanotube sheet.
Figure 14D:
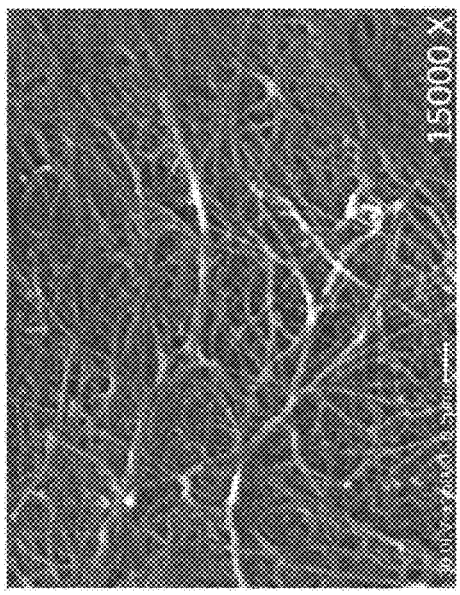
FIG. 14d is a higher magnification scanning electron micrograph of the sheet of FIG. 14c.

FIG. 14a is a scanning electron micrograph of a strained carbon nanotube composite sheet, FIG. 14b is a higher magnification scanning electron micrograph of the sheet of FIG. 14a, FIG. 14c is a scanning electron micrograph of an unstrained carbon nanotube sheet, FIG. 14d is a higher magnification scanning electron micrograph of the sheet of FIG. 14c. As can be seen in the micrographs, the nanotubes or nanotube bundles in the strained sheet have greater alignment than in the unstrained sheet.

Figure 15B:
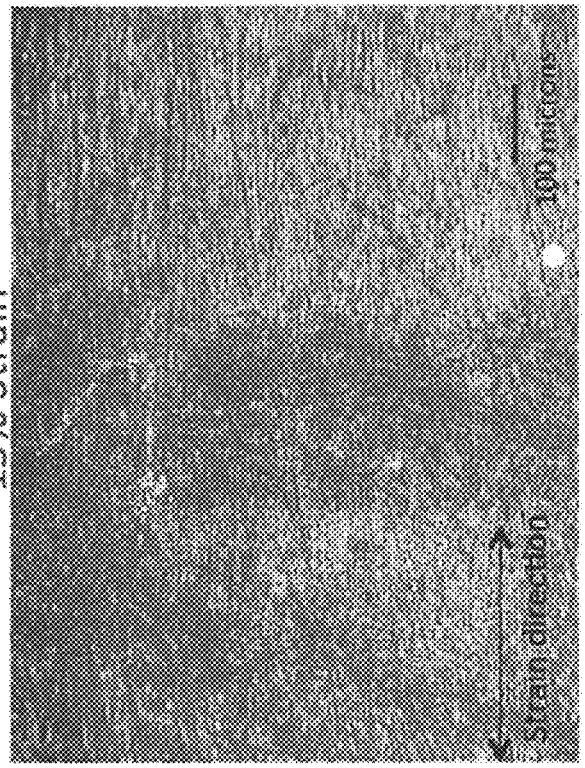
FIG. 15b is an optical micrograph of a carbon nanotube composite sheet with 13% strain.
Figure 15A:
FIG. 15a is an optical micrograph of an unstrained carbon nanotube composite sheet.

FIG. 15a is an optical micrograph of an unstrained carbon nanotube composite sheet, FIG. 15b is an optical micrograph of a carbon nanotube composite sheet with 13% strain.

Figure 16A:
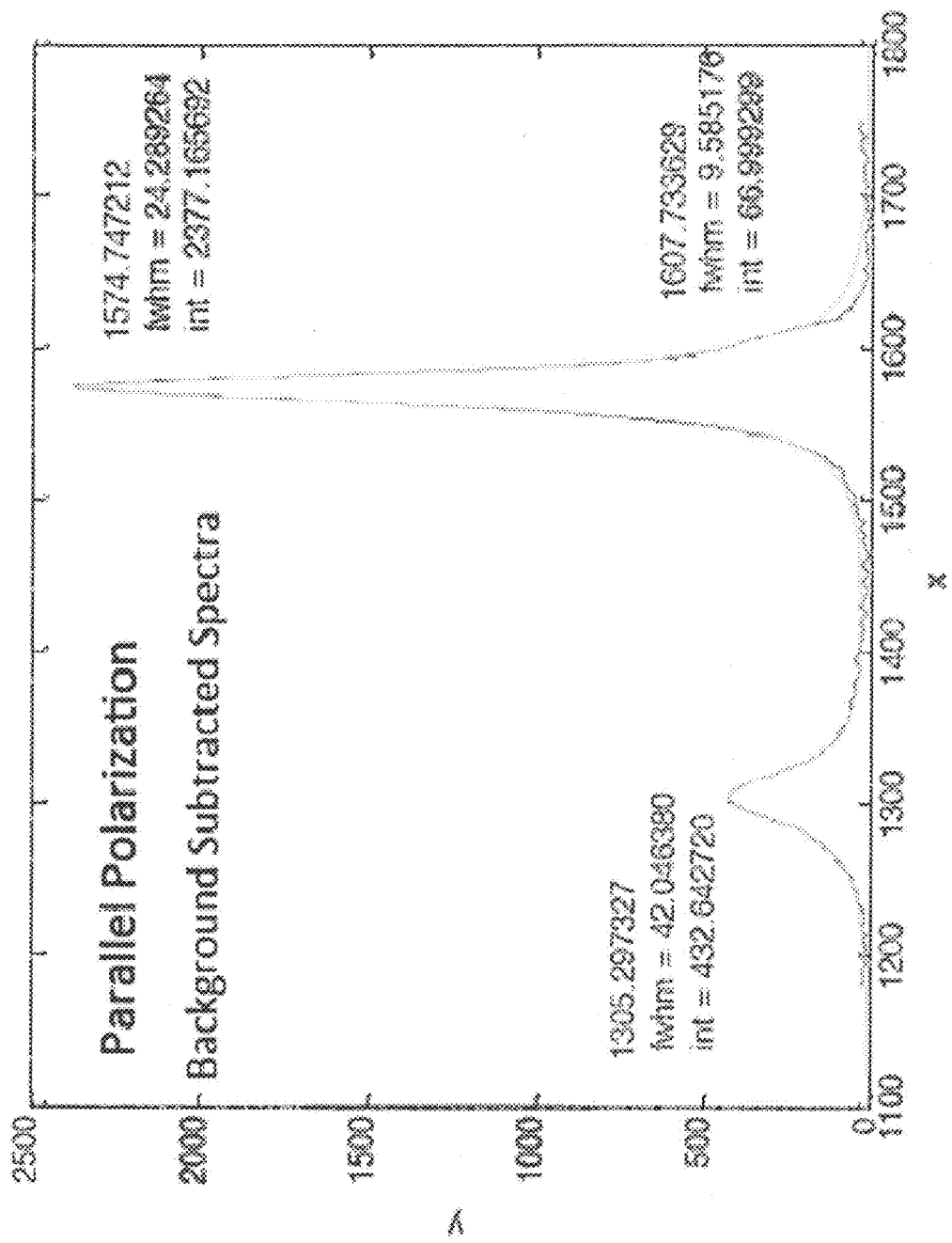
FIG. 16a is a plot illustrating a Raman spectra of a carbon nanotube composite sheet using parallel polarization.
Figure 16B:
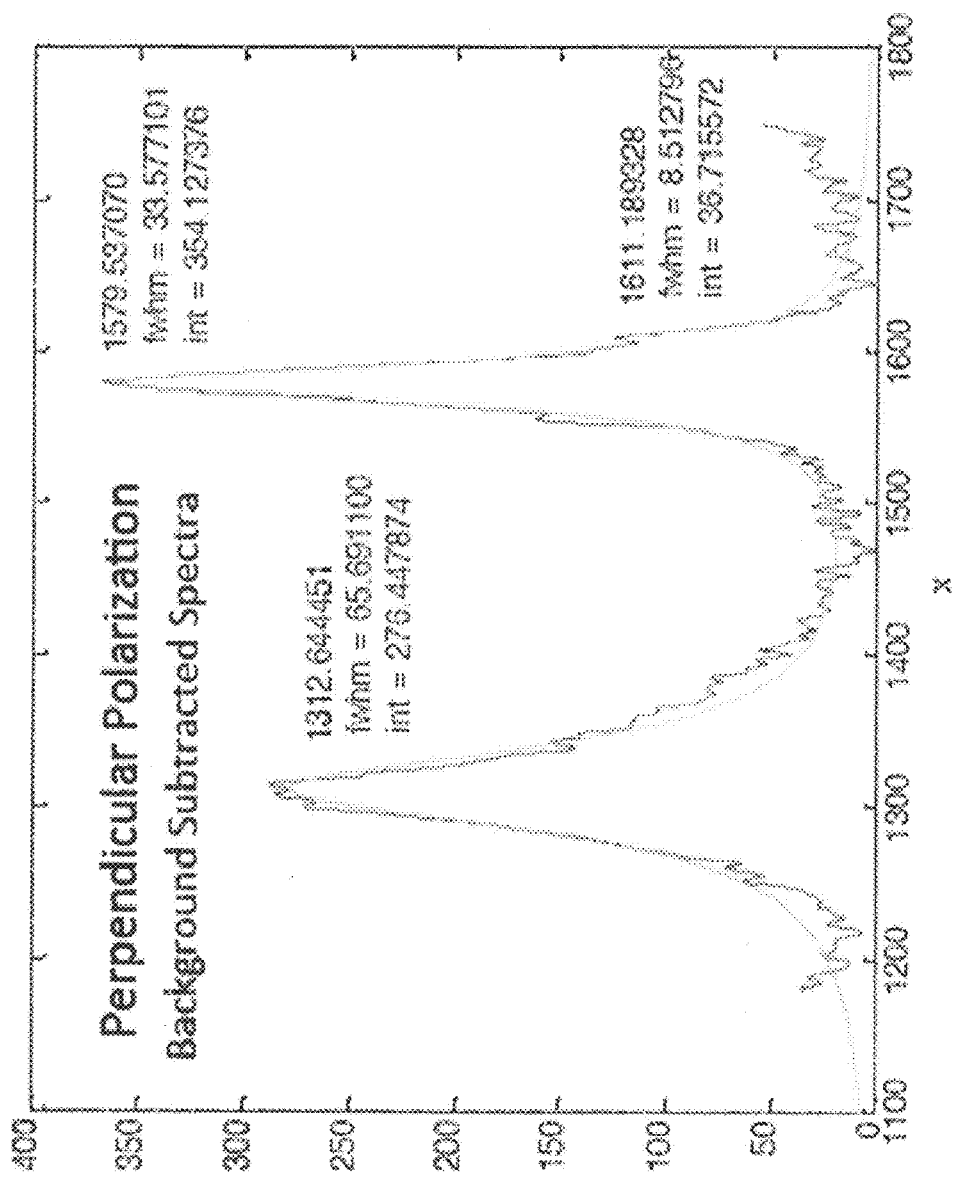
FIG. 16b is a plot illustrating a Raman spectra of the carbon nanotube composite sheet of FIG. 16a using perpendicular polarization.

FIG. 16a illustrates a Raman spectra of a carbon nanotube composite sheet using parallel polarization. FIG. 16b illustrates a Raman spectra of the carbon nanotube composite sheet of FIG. 16a using perpendicular polarization.

Figure 17B:
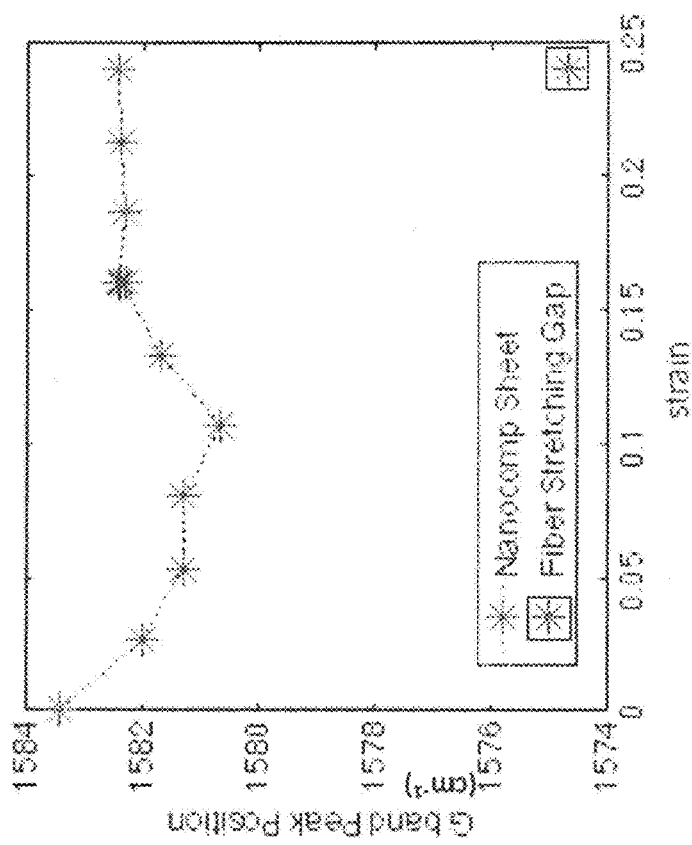
Figure 17A:
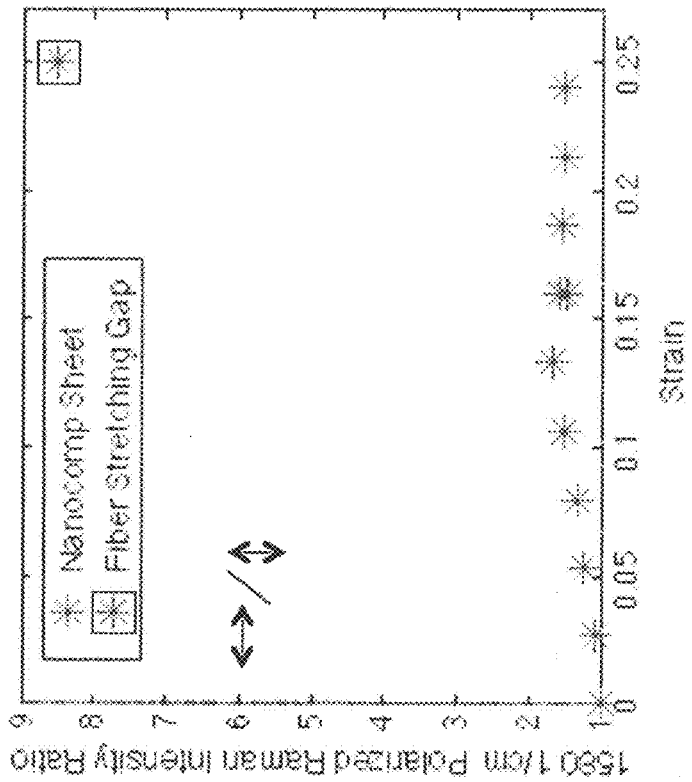
FIG. 17a is a plot of polarized Raman intensity as a function of strain of a carbon nanotube bridging a failure gap in a nanotube composite.

FIG. 17a is a plot of polarized Raman intensity as a function of strain of a carbon nanotube bridging a failure gap in a nanotube composite. FIG. 17b is a plot illustrating the G+ downshift of the carbon nanotube of FIG. 17a. As illustrated in FIG. 17a, the fiber bridging the gap in the sheet has a higher polarized Raman intensity, indicating higher alignment. FIG. 17b shows that the fiber bridging the gap has a greater Raman downshift, indicating higher strain. The G+ downshift of 8.75 cm illustrated in FIG. 17b equates to a stress of 3.125 GPa.

Figure 19A:
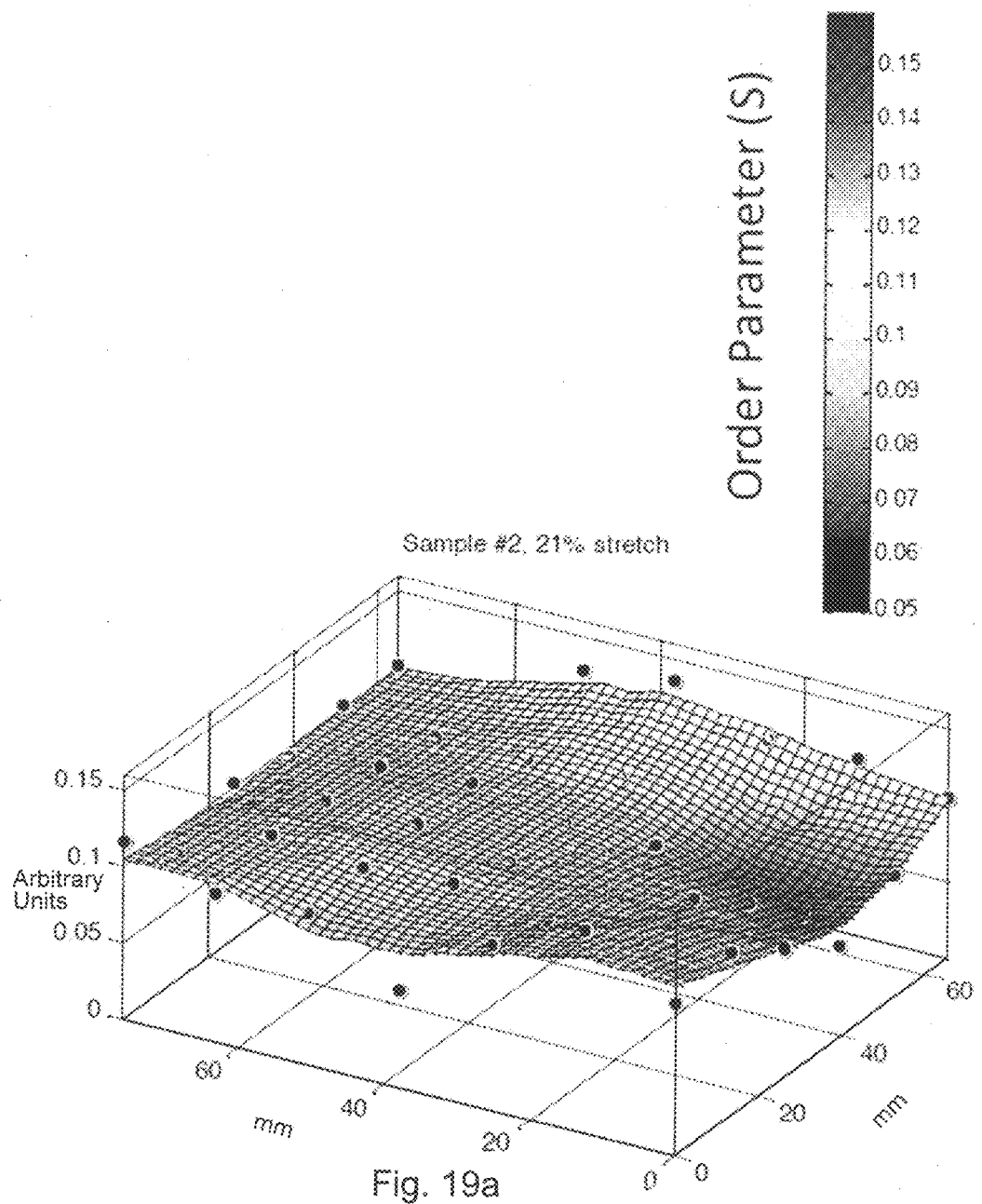
FIG. 19a is an area map illustrating the strain in a 21% stretched carbon nanotube sheet.
Figure 19B:
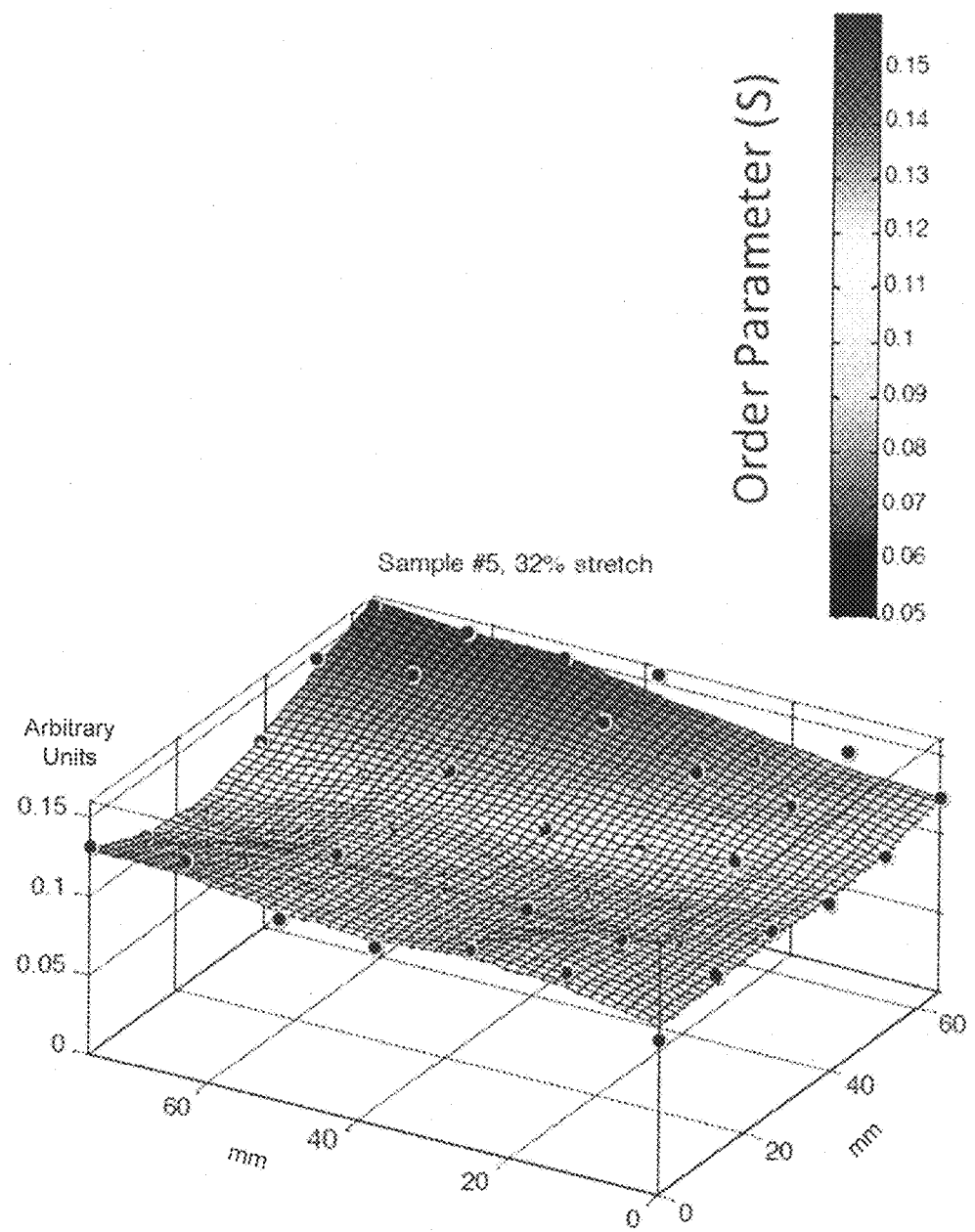
FIG. 19b is an area map illustrating the strain in a 32% stretched carbon nanotube sheet.
Figure 19C:
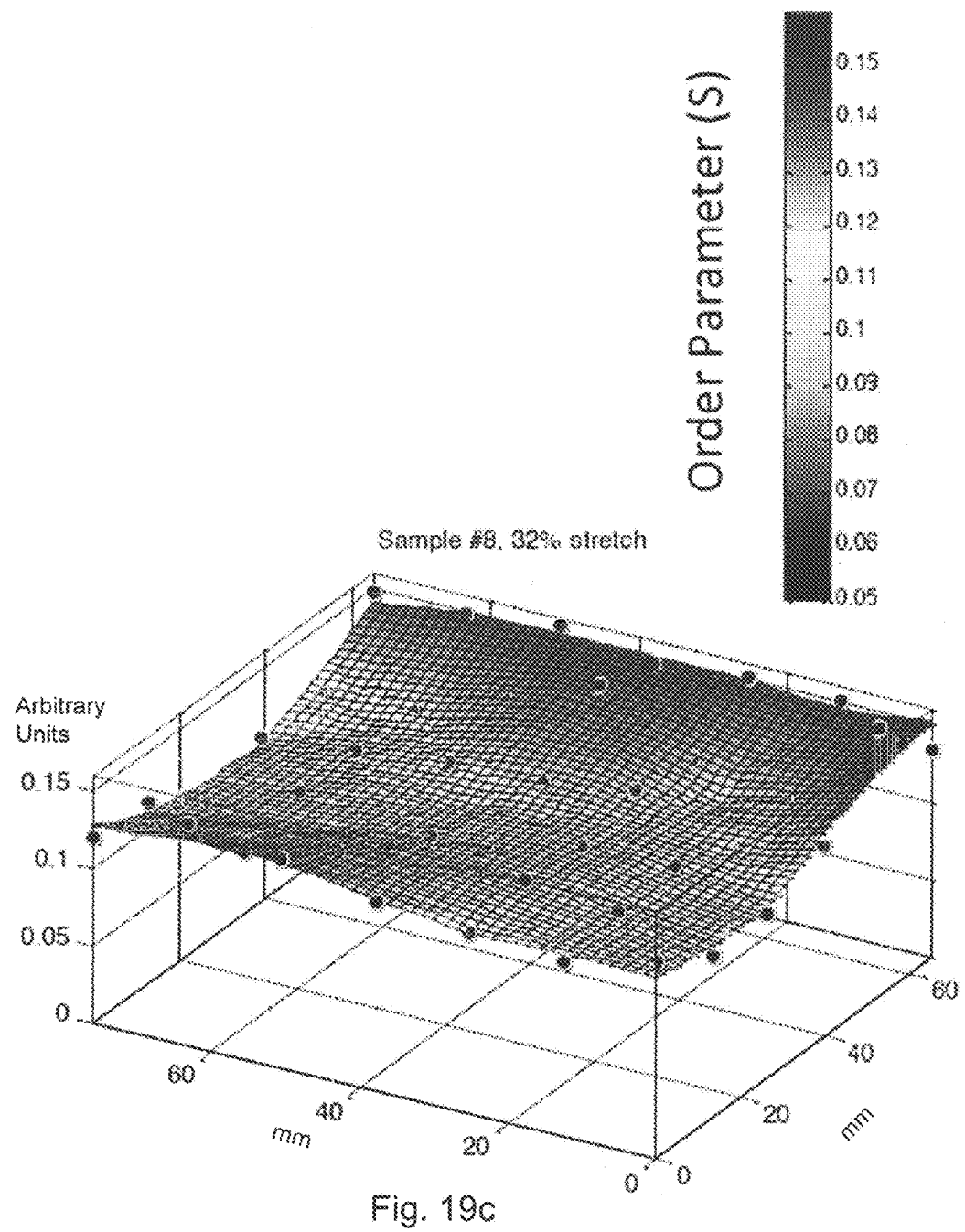
FIG. 19c is an area map illustrating the strain in another 32% stretched carbon nanotube sheet.
Figure 20:
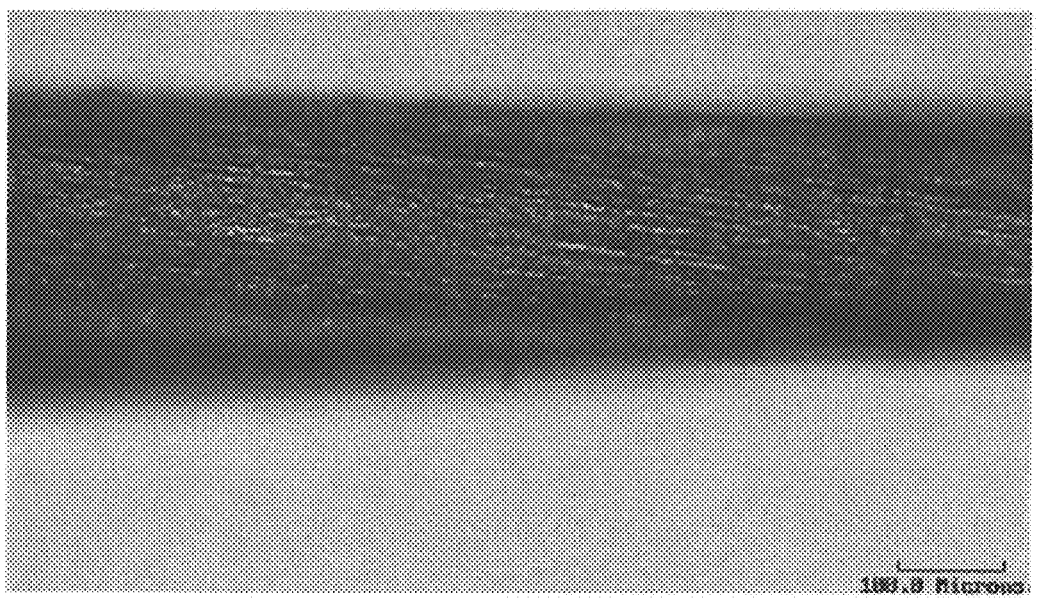
FIG. 20 is a photograph a carbon nanotube yarn starting material.

FIG. 19a is an area map illustrating the relative alignment via the order parameter in a 21% stretched carbon nanotube sheet; FIG. 19b is an area map illustrating the relative alignment in a 32% stretched carbon nanotube sheet, FIG. 20c is an area map illustrating the relative alignment in another 32% stretched carbon nanotube sheet;

FIG. 20 is a photograph a carbon nanotube yarn starting material.

Carbon nanotube based structural materials are being developed as a potential technology for super-strong, aerospace-grade carbon nanotube based structural materials. Incredibly strong at the nanoscale, nanotube based materials are beginning to show the capability to sustain several GPa-level stresses at macroscopic lengths as evidence by recent work. The ability of the nanotube based materials to sustain stresses of this magnitude shows that they can be competitive with state-of-the-art carbon fibers. As discussed herein, a magnetic technique for residual catalyst characterization is demonstrated along with Raman spectroscopy based methods for characterization of nanotube alignment and strain transfer. The techniques may be used to perform material characterization and to provide real-time optimization of process parameters for the fabrication of a structural nanotube composite with high strength-to-weight ratio exceeding current state-of-the-art carbon fiber composites.

The preceding description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the following claims and the principles and novel features disclosed herein.

What is claimed is:

1. A method for process control during fabrication of carbon nanotube structures, the method comprising:
   providing a carbon nanotube starting material;
   forming a composite structure with the carbon nanotube starting material under one or more fabrication process parameters to achieve a desired alignment of individual carbon nanotubes, wherein forming the composite structure comprises:
   monitoring a first property of the composite structure with polarized Raman spectroscopy to characterize the alignment of individual carbon nanotubes, S, as described by the formula, $$S = \tfrac{1}{2}(3\cos^2\beta - 1),$$

wherein, $\beta$ is the angle between the nanotubes and a plurality of measurement axes,
   adjusting the one or more fabrication process parameters if the desired alignment of individual carbon nanotubes is not obtained.

2. The method of claim 1, wherein said monitoring the Raman property of the composite structure is conducted in real time during formation of the composite structure.

3. The method of claim 1, wherein said monitoring the Raman property of the composite structure is completed within about 5-15 seconds.

4. The method of claim 1, wherein said forming a composite structure further comprises achieving a desired strain transfer between the individual carbon nanotubes in the composite structure.

5. The method of claim 4, wherein monitoring a property of the composite structure further comprises monitoring a second property of the composite structure comprising at least one of a G band, a D band, a G' band or radial breathing modes.

6. The method of claim 1, wherein forming a composite structure further comprises:
   monitoring a magnetic property of the composite structure while forming the composite structure, and
   determining the amount and size of at least one residual catalyst in the composite structure during fabrication.

7. The method of claim 6, wherein the at least one residual catalyst comprises a transition metal.

8. The method of claim 7, wherein the transition metal is chosen from the group consisting of: iron, cobalt and nickel.

9. The method of claim 7, wherein the transition metal comprises iron.

10. An in-situ, real time method for process control during fabrication of carbon nanotube structures, the method comprising:
    providing a carbon nanotube starting material;
    forming a composite structure with the carbon nanotube starting material under one or more fabrication process parameters to achieve a desired alignment of individual carbon nanotubes and a desired strain transfer between the individual carbon nanotubes, wherein forming the composite structure comprises:
    monitoring the composite structure with polarized Raman spectroscopy to characterize the alignment of individual carbon nanotubes,
    monitoring the composite structure with polarized Raman spectroscopy to determine a strain transfer between the individual carbon nanotubes, adjusting the one or more fabrication process parameters if the desired alignment of the individual carbon nanotubes or strain transfer between the individual carbon nanotubes is not obtained;

continuing formation of the composite structure if the desired alignment of the individual carbon nanotubes and strain transfer between the individual carbon nanotubes is obtained.

11. The method of claim 10, wherein monitoring the composite structure with polarized Raman spectroscopy to characterize the alignment of individual carbon nanotubes, S, as described by the formula, $$S = \tfrac{1}{2}(3\cos^2\beta - 1),$$

wherein, $\beta$ is the angle between the nanotubes and a plurality of measurement axes.

12. The method of claim 11, wherein monitoring the composite structure with polarized Raman spectroscopy to determine a strain transfer between the individual carbon nanotubes comprises determining a G band, a D band, a G' band or radial breathing modes.

13. A method for process control during fabrication of carbon nanotube structures, the method comprising:

providing a carbon nanotube starting material;

forming the composite structure with the carbon nanotube starting material under one or more fabrication process parameters; and monitoring a magnetic property of the composite structure while forming the composite structure.

14. The method of claim 13, wherein monitoring the magnetic property comprises determining the amount and size of at least one residual catalyst in the composite structure during fabrication.

15. The method of claim 14, wherein the catalyst comprises a transition metal.

16. The method of claim 15, wherein the transition metal is chosen from the group consisting of: iron, nickel or cobalt.

17. The method of claim 15, wherein the transition metal comprises iron.

18. The method of claim 13, further comprising:

determining a desired size and amount of residual catalyst in the composite structure to optimize the strength of the composite structure, adjusting the one or more fabrication process parameters if the desired size and amount of the residual catalyst is not obtained;

continuing formation of the composite structure if the desired size and amount of the residual catalyst is obtained.

19. The method of claim 18, wherein the magnetic property is monitored with a semiconducting quantum interference device.

20. The method of claim 13, wherein forming the composite structure comprises exposing the carbon nanotube starting material to a solvent.

* * * * *